United States Patent [19]

Marco et al.

[11] Patent Number: 5,792,932
[45] Date of Patent: Aug. 11, 1998

[54] PLANT PROMOTER, MICROORGANISMS AND PLANT CELLS CONTAINING A UNIT FOR THE EXPRESSION OF A PROTEIN OF INTEREST COMPRISING SAID PROMOTER

[75] Inventors: Yves Marco, Castanet-Tolosan; Dominique Roby; Michel Schneider, both of Toulouse; Alain Toppan, Cornebarrieu, all of France

[73] Assignee: Rustica Prograin Genetique, Mondonville, France

[21] Appl. No.: 525,507

[22] PCT Filed: Mar. 23, 1994

[86] PCT No.: PCT/FR94/00316

§ 371 Date: Sep. 22, 1995

§ 102(e) Date: Sep. 22, 1995

[87] PCT Pub. No.: WO94/21793

PCT Pub. Date: Sep. 29, 1994

[30] Foreign Application Priority Data

Mar. 23, 1993 [FR] France .................................. 93 03299

[51] Int. Cl.⁶ .............................. C07H 21/04; C12N 1/00; C12N 1/21; C12N 5/14; C12N 15/82
[52] U.S. Cl. ...................... 800/205; 435/172.3; 435/243; 435/252.3; 435/320.1; 435/419; 536/24.1; 800/250
[58] Field of Search ...................... 800/205, 250; 435/240.4, 320.1, 172.3, 6, 252.3; 536/24.1; 424/93.21

[56] References Cited

PUBLICATIONS

Bodwell, et al. in Computational Molecular Biology (Lesk. ed.) Oxford University Press, Oxford, 1988, pp. 170–171.

*Primary Examiner*—Douglas W. Robinson
*Assistant Examiner*—Amy J. Nelson
*Attorney, Agent, or Firm*—Dennison, Meserole, Pollack & Scheiner

[57] ABSTRACT

The present invention relates to a plant promoter which comprises the sequence (B) [SEQ ID NO: 4] below:

```
TCAAATGAAA TACACATAAG AAGCACATAA
       ATTTAAATGC CGTATTAAAC TTACAGTATA    60

CTATAGCGGA AGTTGGCTTG ATAAAGGAAC
       GCTGAGGAGA GTAGCCGATG GTGAAACACT   120

AACATCAAGT GCAAAAGAAA GAAAAACTGA
       AAACAGAAGA TGAATGTTTG AAGTGGGTAA   180

AAGATTACTT AAAAGATAGG TTTGGTTAAC

-continued
       AAATGATTGT GACTGTTACG AAGCAGTGTG   240

AACCGTTGGG ACTTTTAATA TTCTTCGGCA
       GAAGAACATT GCTCTTTCAA CGTATGTAGT   300
CTTTGTCTAC TTGTAGTTTT TTTTAATTTA
       AATTAAATAA GTTAATTAGA GAAATAATAA   360

GAAGGATATT TTAGTAATTC AACTTTTAAC
       TTTTAGGTTT CCCACTTATA ATATAATATA   420

GATATAGTTT TTTTTAATTT AAATTAAATA
       AGTTAATTAG AGAAATAATA AGAAGGATAT   480

TTTAGTAATT CAACTTTTAA CTTTTAGGGT
       TTCCACTTAT AATATAATAT AGATATAGAT   540

ATAGATATAG ATATAGATAA AGATATATAG
       ATATAGATAG ATAATATAGA TGGATGAGTC   600

ATTGGCGATA AAGTGAGGAT TGTTTCATTT
       TTGTTATTAA AAACTTACTA CTCCTTAAAT   660

ATAAAATATG ATTCCTTTTA AAAAAGAAAT
       AGAATAAAAA TAAAGATAAA ACACTAAAAA   720

TAAATTAATT GTCTAGACAA AATCTACCGT
       TCACCTCAAT TAATACACAT CCCCGTCCAC   780

ATCATGAAGT AGCTAGCACA AGCGTACAGA
       TCAGTTGAAA GAAGAAAAGG GTCCAGTCCT   840

AAATATCCAA ATGTTCATGA AAGGAGGACA
       ACTTAGTTTT TTCTACTAGA AAGAATATTT   900

TGACGAATTT CGTTCACATT GGCATGCTTT
       AATTATATTA AGTAGTCTTT CTTGGAAAAG   960

AAGTATTTGC AATATCAAAC CAAATCTTCC
       CATTACGCAA GCAATGACAT CTAAGCAAAT  1020

ATATATCACT ATAAATAGTA CTACTAATGT
       TCAATGACTT TTATAAGCAC TACATATATA  1080

T ACTCAAACA AAAAGA                     1096
``` or a sequence having a high degree of homology with the sequence (B).

Application: Protection of plants by genetic engineering and especially defense of plants in stress conditions

13 Claims, 4 Drawing Sheets

```
   1 ..............................ACGTATGTAGTC   12
                                    ||||||||||||
1301 CTTTTAATATTCTTCGGCAGAAGAACATTGCTCTTTCCACGTATGTAGTC 1350

13 TTTGTCTACTTGTAGTTTTTTTAATTTAAATTAAATAAGTTAATTAGAG   62
     |||||||||||||||||||||||||||||||||||||||||||||||||
1351 TTTGTCTACTTGTAGTTTTTTTAATTTAAATTAAATAAGTTAATTAGAG  1400

63 AAATAATAAGAAGGATATTTAGTAATTCAACTTTTAACTTTTAGGTTTC  112
     |||||||||||||||||||||||||||||||||||||||||||||||||
1401 AAATAATAAGAAGGATATTTAGTAATTCAACTTTTAACTTTTAGGTTTC  1450

113 CCACTTATAATATAATATA GATATAGTTTTTTTAATTTAAATTAAATAA  162
     ||||||||||||||||||| |||||||||||||||||||||||||||||
1451 CCACTTATAATATAATATAGATATAGTTTTTTTAATTTAAATTAAATAA  1500

163 GTTAATTAGAGAAATAATAAGAAGGATATTTAGTAATTCAACTTTTAAC  212
     |||||||||||||||||||||||||||||||||||||||||||||||||
1501 GTTAATTAGAGAAATAATAAGAAGGATATTTAGTAATTCAACTTTTAAC  1550

213 TTTTAGGGTTTCCACTTATAATATAATATAGATATAGATATAGATATAGA  262
     |||||||||||||||||||||||||||||||||||||||||||||||||
1551 TTTTAGGGTTTCCACTTATAATATAATATAGATATAGATATAGATATAGA  1600

263 TATAGATAAAGATATATAGATATAGATAGATAATATAGATGGATGAGTC  312
     |||||||  ||||||||||||||||||||||||||||||||||||||||
1601 TATAGAT.AAAGATATATAGATATAGATAGATAATATAGATGGATGAGTC 1649

313 ATTGGCGATAAAGTGAGGA.TGTTTCATTTTGTTATTAAAAACTTACTA  361
     |||||||||||||||||||  ||||||||||||||||||||||||||||
1650 ATTGGCGATAAAGTGAGGATTGTTTCATTTTGTTATTAAAAACTTACTA  1699

362 CTCCTTAAATATAAAATATGATTCCTTTTAAAAAGAAATAGAATAAAAA  411
     |||||||||||||||||||||||||||||||||||||||||||||||||
1700 CTCCTTAAATATAAAATATGATTCCTTTTAAAAAGAAATAGAATAAAAA  1749

412 TAAAGATAAAACACTAAAAATAAATTAATTGTCTAGACAAAATCTACCGT  461
     |||||||||||||||||||||||||||||||||||||||||||||||||
1750 TAAAGATAAAACACTAAAAATAAATTAATTGTCTAGACAAAATCTACCGT  1799
```

FIG. 2(a)

```
462   TCACCTCAATTAATACACATCCCCGTCCACATCATGAAGTAGCTAGCACA   511
      ||||||||||||||||||||||||||||||||||||||||||||||||||
1800  TCACCTCAATTAATACACATCCCCGTCCACATCATGAAGTAGCTAGCACA   1849

512   AGCGTACAGATCAGTTGAAAGAAGAAAAGGGTCCAGTCCTAAATATCCAA   561
      ||||||||||||||||||||||||||||||||||||||||||||||||||
1850  AGCGTACAGATCAGTTGAAAGAAGAAAAGGGTCCAGTCCTAAATATCCAA   1899

562   ATGTTCATGAAAGGAGGACAACTTAGTTTTTTCTACTAGAAAGAATATTT   611
      ||||||||||||||||||||||||||||||||||||||||||||||||||
1900  ATGTTCATGAAAGGAGGACAACTTAGTTTTTTCTACTAGAAAGAATATTT   1949

612   TGACGAATTTCGTTCACATTGGCATGCTTTAATT.TATTAAGTAGTCTTT   660
      |||||||||||||||||||||||||||||||||| |||||||||||||||
1950  TGACGAATTTCGTTCACATTGGCATGCTTTAATTATATTAAGTAGTCTTT   1999

661   CTTGGAAAAGAAGTATTTGCAATATCAAACCAAATCTTCCCATTACGCAA   710
      ||||||||||||||||||||||||||||||||||||||||||||||||||
2000  CTTGGAAAAGAAGTATTTGCAATATCAAACCAAATCTTCCCATTACGCAA   2049

711   GCAATGACATCTAAGCAAATATATATCACTATAAATAGTACTACTAATGT   760
      ||||||||||||||||||||||||||||||||||||||||||||||||||
2050  GCAATGACATCTAAGCAAATATATATCACTATAAATAGTACTACTAATGT   2099

761   TCAATGACTTTTATAAGCACTACATATATATTCTCAAACAAAAAGA      806
      |||||||||||||||||||||||||||||||||| |||||||||||
2100  TCAATGACTTTTATAAGCACTACATATATATACTCAAACAAAAAGA      2145
```

FIG. 2(b)

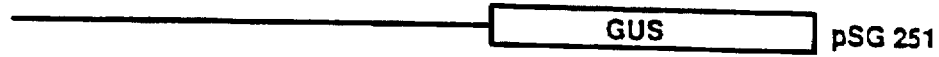
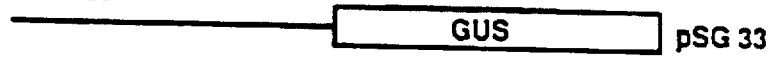
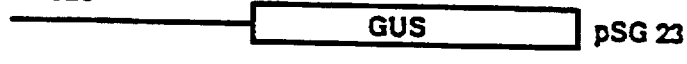
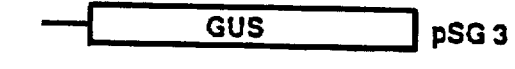
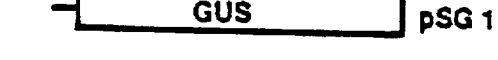
FIG. 3

SEQUENCE LISTING ( 1 ) GENERAL INFORMATION:

( i i i ) NUMBER OF SEQUENCES:18

( 2 ) INFORMATION FOR SEQ ID NO: 1:

( i ) SEQUENCE CHARACTERISTICS:
        ( A ) LENGTH: 631 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i i ) IMMEDIATE SOURCE:
        ( B ) CLONE: 246

( i x ) FEATURE:
        ( A ) NAME/KEY: CDS
        ( B ) LOCATION:join(1..177, 368..631)

( i x ) FEATURE:
        ( A ) NAME/KEY: intron
        ( B ) LOCATION:178..367

( i x ) FEATURE:
        ( A ) NAME/KEY: misc_signal
        ( B ) LOCATION:175..182
        ( D ) OTHER INFORMATION:/function="consensus spicing sequences"

( i x ) FEATURE:
        ( A ) NAME/KEY: misc_signal
        ( B ) LOCATION:323..333
        ( D ) OTHER INFORMATION:/function="consensus spicing sequences"

( i x ) FEATURE:
        ( A ) NAME/KEY: misc_signal
        ( B ) LOCATION:363..368
        ( D ) OTHER INFORMATION:/function="consensus spicing sequences"

( x i ) SEQUENCE DESCRIPTION: SEQ ID NO: 1:

```
ATG  AAC  CCT  GTT  CAC  AAA  AAG  ATC  CCT  ATT  TTG  ATT  CAC  AAT  AGT  AAA           48
Met  Asn  Pro  Val  His  Lys  Lys  Ile  Pro  Ile  Leu  Ile  His  Asn  Ser  Lys
 1              5                        10                       15

GCC  ATT  TGT  GAG  TCT  CTA  AAC  ATT  CTT  GAG  TAC  ATT  GAT  GAA  GTC  TGG           96
Ala  Ile  Cys  Glu  Ser  Leu  Asn  Ile  Leu  Glu  Tyr  Ile  Asp  Glu  Val  Trp
               20                        25                       30

CAT  GAC  AAA  TGT  CCA  TTA  CTT  CCT  TCT  GAT  CCT  TAC  GAA  AAG  TCA  CAA          144
His  Asp  Lys  Cys  Pro  Leu  Leu  Pro  Ser  Asp  Pro  Tyr  Glu  Lys  Ser  Gln
          35                        40                       45

GCC  AGA  TTC  TGG  GCC  GAC  TAT  ATT  GAC  AAG  AAG  GTAATAAACA  TCTCACAAAG          197
Ala  Arg  Phe  Trp  Ala  Asp  Tyr  Ile  Asp  Lys  Lys
     50                        55

ACTTAACAGT  CAATGTAACA  TGACCTTTAC  TAAGTTCATC  TTGTGTAGTT  TCACCGAGCT             257

GTTTAAGGTC  GTCGTACATT  TGAATATTAG  GTGTTTCACA  TTTGAATTTT  TTTATCCCCT             317

TGTTAGAATT  CCTGATTCTG  TCAATACTTA  TGGACGTTGG  TTTAATGCAG  ATA  TAT              373
                                                             Ile  Tyr
                                                              60
```

```
AGC  ACA  GGA  AGA  AGA  GTG  TGG  AGC  GGT  AAA  GGT  GAA  GAT  CAA  GAA  GAA         421
Ser  Thr  Gly  Arg  Arg  Val  Trp  Ser  Gly  Lys  Gly  Glu  Asp  Gln  Glu  Glu
               65                        70                       75

GCA  AAG  AAG  GAA  TTC  ATA  GAA  ATA  CTC  AAG  ACT  TTG  GAA  GGA  GAG  CTT         469
Ala  Lys  Lys  Glu  Phe  Ile  Glu  Ile  Leu  Lys  Thr  Leu  Glu  Gly  Glu  Leu
          80                        85                       90

GGA  AAT  AAA  ACT  TAC  TTT  GGT  GGT  GAT  AAT  CTG  GGT  TTT  GTG  GAT  GTG         517
Gly  Asn  Lys  Thr  Tyr  Phe  Gly  Gly  Asp  Asn  Leu  Gly  Phe  Val  Asp  Val
          95                       100                      105

GCT  TTG  GTT  CCC  TTT  ACT  AGT  TGG  TTT  TAT  TCT  TAT  GAG  ACT  TGT  GCA         565
Ala  Leu  Val  Pro  Phe  Thr  Ser  Trp  Phe  Tyr  Ser  Tyr  Glu  Thr  Cys  Ala
110                      115                      120                      125

AAC  TTT  AGT  ATA  GAA  GCA  GAG  TGT  CCA  AAG  CTG  GTG  GTA  TGG  GCA  AAA         613
Asn  Phe  Ser  Ile  Glu  Ala  Glu  Cys  Pro  Lys  Leu  Val  Val  Trp  Ala  Lys
               130                      135                      140

ACA  TGT  ATG  GAG  AGC  GAG                                                            631
Thr  Cys  Met  Glu  Ser  Glu
               145
```

( 2 ) INFORMATION FOR SEQ ID NO: 2:

( i ) SEQUENCE CHARACTERISTICS:
        ( A ) LENGTH: 147 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
Met  Asn  Pro  Val  His  Lys  Lys  Ile  Pro  Ile  Leu  Ile  His  Asn  Ser  Lys
 1                        5                        10                       15

Ala  Ile  Cys  Glu  Ser  Leu  Asn  Ile  Leu  Glu  Tyr  Ile  Asp  Glu  Val  Trp
               20                       25                       30

His  Asp  Lys  Cys  Pro  Leu  Leu  Pro  Ser  Asp  Pro  Tyr  Glu  Lys  Ser  Gln
          35                       40                       45

Ala  Arg  Phe  Trp  Ala  Asp  Tyr  Ile  Asp  Lys  Lys  Ile  Tyr  Ser  Thr  Gly
     50                       55                       60

Arg  Arg  Val  Trp  Ser  Gly  Lys  Gly  Glu  Asp  Gln  Glu  Glu  Ala  Lys  Lys
65                        70                       75                       80

Glu  Phe  Ile  Glu  Ile  Leu  Lys  Thr  Leu  Glu  Gly  Glu  Leu  Gly  Asn  Lys
                    85                       90                       95

Thr  Tyr  Phe  Gly  Gly  Asp  Asn  Leu  Gly  Phe  Val  Asp  Val  Ala  Leu  Val
               100                      105                      110

Pro  Phe  Thr  Ser  Trp  Phe  Tyr  Ser  Tyr  Glu  Thr  Cys  Ala  Asn  Phe  Ser
          115                      120                      125

Ile  Glu  Ala  Glu  Cys  Pro  Lys  Leu  Val  Val  Trp  Ala  Lys  Thr  Cys  Met
     130                      135                      140

Glu  Ser  Glu
145
```

( 2 ) INFORMATION FOR SEQ ID NO: 3:

( i ) SEQUENCE CHARACTERISTICS:
        ( A ) LENGTH: 441 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i i ) IMMEDIATE SOURCE:
    ( B ) CLONE: 246

( x i ) SEQUENCE DESCRIPTION: SEQ ID NO: 3:

```
ATGAACCCTG  TTCACAAAAA  GATCCCTATT  TTGATTCACA  ATAGTAAAGC  CATTTGTGAG    60
TCTCTAAACA  TTCTTGAGTA  CATTGATGAA  GTCTGGCATG  ACAAATGTCC  ATTACTTCCT   120
TCTGATCCTT  ACGAAAAGTC  ACAAGCCAGA  TTCTGGGCCG  ACTATATTGA  CAAGAAGATA   180
TATAGCACAG  GAAGAAGAGT  GTGGAGCGGT  AAAGGTGAAG  ATCAAGAAGA  AGCAAAGAAG   240
GAATTCATAG  AAATACTCAA  GACTTTGGAA  GGAGAGCTTG  GAAATAAAAC  TTACTTTGGT   300
GGTGATAATC  TGGGTTTTGT  GGATGTGGCT  TTGGTTCCCT  TTACTAGTTG  GTTTTATTCT   360
TATGAGACTT  GTGCAAACTT  TAGTATAGAA  GCAGAGTGTC  CAAAGCTGGT  GGTATGGGCA   420
AAAACATGTA  TGGAGAGCGA  G                                                441
```

( 2 ) INFORMATION FOR SEQ ID NO: 4:

( i ) SEQUENCE CHARACTERISTICS:
        ( A ) LENGTH: 1096 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO: 4:

```
TCAAATGAAA  TACACATAAG  AAGCACATAA  ATTTAAATGC  CGTATTAAAC  TTACAGTATA    60
CTATAGCGGA  AGTTGGCTTG  ATAAAGGAAC  GCTGAGGAGA  GTAGCCGATG  GTGAAACACT   120
AACATCAAGT  GCAAAGAAA   GAAAAACTGA  AAACAGAAGA  TGAATGTTTG  AAGTGGGTAA   180
AAGATTACTT  AAAAGATAGG  TTTGGTTAAC  AAATGATTGT  GACTGTTACG  AAGCAGTGTG   240
AACCGTTGGG  ACTTTTAATA  TTCTTCGGCA  GAAGAACATT  GCTCTTTCCA  CGTATGTAGT   300
CTTTGTCTAC  TTGTAGTTTT  TTTTAATTTA  AATTAAATAA  GTTAATTAGA  GAAATAATAA   360
GAAGGATATT  TTAGTAATTC  AACTTTTAAC  TTTTAGGTTT  CCCACTTATA  ATATAATATA   420
GATATAGTTT  TTTTTAATTT  AAATTAAATA  AGTTAATTAG  AGAAATAATA  AGAAGGATAT   480
TTAGTAATT   CAACTTTTAA  CTTTTAGGGT  TTCCACTTAT  AATATAATAT  AGATATAGAT   540
ATAGATATAG  ATATAGATAA  AGATATATAG  ATATAGATAG  ATAATATAGA  TGGATGAGTC   600
ATTGGCGATA  AAGTGAGGAT  TGTTTCATTT  TTGTTATTAA  AAACTTACTA  CTCCTTAAAT   660
ATAAAATATG  ATTCCTTTTA  AAAAGAAAT   AGAATAAAAA  TAAAGATAAA  ACACTAAAAA   720
TAAATTAATT  GTCTAGACAA  AATCTACCGT  TCACCTCAAT  TAATACACAT  CCCCGTCCAC   780
ATCATGAAGT  AGCTAGCACA  AGCGTACAGA  TCAGTTGAAA  GAAGAAAGG   GTCCAGTCCT   840
AAATATCCAA  ATGTTCATGA  AAGGAGGACA  ACTTAGTTTT  TTCTACTAGA  AAGAATATTT   900
TGACGAATTT  CGTTCACATT  GGCATGCTTT  AATTATATTA  AGTAGTCTTT  CTTGGAAAAG   960
AAGTATTTGC  AATATCAAAC  CAAATCTTCC  CATTACGCAA  GCAATGACAT  CTAAGCAAAT  1020
ATATATCACT  ATAAATAGTA  CTACTAATGT  TCAATGACTT  TTATAAGCAC  TACATATATA  1080
TACTCAAACA  AAAAGA                                                      1096
```

( 2 ) INFORMATION FOR SEQ ID NO: 5:

( i ) SEQUENCE CHARACTERISTICS:
        ( A ) LENGTH: 236 base pairs
        ( B ) TYPE: nucleic acid (C) STRANDEDNESS: single
(D) TOPOLOGY: linear (ii) MOLECULE TYPE: DNA (genomic)

(iii) HYPOTHETICAL: NO (xi) SEQUENCE DESCRIPTION: SEQ ID NO: 5:

| | | | | | |
|---|---|---|---|---|---|
| CCTTTTTCGA | TTCTAATCCA | ATCAATTCAA | CAGTGTAAGG | TGAAGCAGTC | AATTTAAAGG | 60 |
| AAGGCCTTTA | AATTCTAAAA | TATTGTACTT | TTCCTGCGCT | TCTAAAAGTG | AACGACAAAG | 120 |
| AAAAAATAGT | TATTCTTGAA | CTTAATATTG | TACAATAGGA | TAAATTTTAA | CTATCTATAA | 180 |
| AAAGAGAACA | AAACCTTAAT | CTCTTCAAAA | TAATATTATA | AGAAGTAACA | TAATTG | 236 |

(2) INFORMATION FOR SEQ ID NO: 6:

(i) SEQUENCE CHARACTERISTICS:
(A) LENGTH: 813 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (xi) SEQUENCE DESCRIPTION: SEQ ID NO: 6:

| | | | | | |
|---|---|---|---|---|---|
| GAGCTCGGCA | AGGCTGACCA | AAGTCACAGA | AGCGATTGGA | ATTCGCAGGA | CAGACCATGC | 60 |
| ACCTGCGCAC | AAAATGTCGT | AGGTGCGACA | CACCAGAACC | AGCACTGGGC | AGCAGGTTTC | 120 |
| AATTGCTCTG | TGGCTCGTTT | GAAACTCATC | CGAGCCACTC | ATGACCTCGT | CCGAATATTT | 180 |
| CAACAAGTCC | ATAAACATAA | TACGGACATA | CTCGGGGTTT | CACTTCACGT | CAAACAACAT | 240 |
| CAAAATTACA | AATCACACCC | CGATTCGAAC | CTTGAGTTTT | AAACTTTTCA | ATTTGCAAAT | 300 |
| CTCGTGCCAA | AACATATTAA | ATGAATCCGG | AATGACTTCA | AATTTATAAA | TGACATAACG | 360 |
| GAGTTGTTCA | AATTTCCAGA | ATCAGATTCT | GCCTTTGATA | TCAAAAAGTC | AACCCCGTGA | 420 |
| TCAAACTTGG | AATTCTTTAG | CCTTTAAATT | GCTAGTTTTC | GTTAAATGGT | CATAACTTGA | 480 |
| GCTATGGACC | TCCAAATTAA | ATTTCGGGCA | TACGCTCAAA | TCCCAATTAC | GAATACGGAG | 540 |
| CTACCGGACT | GTCAAAATAC | TGATCCGGGT | CCGTTTGCTA | AAAACGTTGA | CCAAAGTCCA | 600 |
| CTAAGTTGAG | TTTTAAAACT | TTATTTCACA | TTTTAATCCA | TTTTTTACAT | GAAAACTTTC | 660 |
| CGGAAAATAC | GGAGTATGCA | CGCAAGTCGA | GGAATGATAA | ATGGTACGTT | TCGAAGTTTT | 720 |
| AGAACTCAAA | ATTACTTATT | AAATTTAAAG | ATGACATTTT | GGGTCATCAC | ATTGATGAAA | 780 |
| ATTTTGACAT | TAATATCTGA | GAACTTTCTT | TGA | | | 813 |

(2) INFORMATION FOR SEQ ID NO: 7:

(i) SEQUENCE CHARACTERISTICS:
(A) LENGTH: 3046 base pairs
(B) TYPE: nucleic acid
(C) STRANDEDNESS: single
(D) TOPOLOGY: linear (ii) MOLECULE TYPE: cDNA (iii) HYPOTHETICAL: NO (vii) IMMEDIATE SOURCE:
(B) CLONE: 246C (xi) SEQUENCE DESCRIPTION: SEQ ID NO: 7:

| | | | | | |
|---|---|---|---|---|---|
| GAGCTCGGCA | AGGCTGACCA | AAGTCACAGA | AGCGATTGGA | ATTCGCAGGA | CAGACCATGC | 60 |

-continued

| | | | | | |
|---|---|---|---|---|---|
| ACCTGCGCAC | AAAATGTCGT | AGGTGCGACA | CACCAGAACC | AGCACTGGGC | AGCAGGTTTC | 120
| AATTGCTCTG | TGGCTCGTTT | GAAACTCATC | CGAGCCACTC | ATGACCTCGT | CCGAATATTT | 180
| CAACAAGTCC | ATAAACATAA | TACGGACATA | CTCGGGGTTT | CACTTCACGT | CAAACAACAT | 240
| CAAAATTACA | AATCACACCC | CGATTCGAAC | CTTGAGTTTT | AAACTTTTCA | ATTTGCAAAT | 300
| CTCGTGCCAA | AACATATTAA | ATGAATCCGG | AATGACTTCA | AATTTATAAA | TGACATAACG | 360
| GAGTTGTTCA | AATTTCCAGA | ATCAGATTCT | GCCTTTGATA | TCAAAAGTC  | AACCCCGTGA | 420
| TCAAACTTGG | AATTCTTTAG | CCTTTAAATT | GCTAGTTTTC | GTTAAATGGT | CATAACTTGA | 480
| GCTATGGACC | TCCAAATTAA | ATTTCGGGCA | TACGCTCAAA | TCCCAATTAC | GAATACGGAG | 540
| CTACCGGACT | GTCAAAATAC | TGATCCGGGT | CCGTTTGCTA | AAAACGTTGA | CCAAAGTCCA | 600
| CTAAGTTGAG | TTTTAAAACT | TTATTTCACA | TTTTAATCCA | TTTTTTACAT | GAAAACTTTC | 660
| CGGAAAATAC | GGAGTATGCA | CGCAAGTCGA | GGAATGATAA | ATGGTACGTT | TCGAAGTTTT | 720
| AGAACTCAAA | ATTACTTATT | AAATTTAAAG | ATGACATTTT | GGGTCATCAC | ATTGATGAAA | 780
| ATTTTGACAT | TAATATCTGA | GAACTTTCTT | TGACCTTTTT | CGATTCTAAT | CCAATCAATT | 840
| CAACAGTGTA | AGGTGAAGCA | GTCAATTTAA | AGGAAGGCCT | TTAAATTCTA | AAATATTGTA | 900
| CTTTTCCTGC | GCTTCTAAAA | GTGAACGACA | AAGAAAAAAT | AGTTATTCTT | GAACTTAATA | 960
| TTGTACAATA | GGATAAATTT | TAACTATCTA | TAAAAGAGA  | ACAAAACCTT | AATCTCTTCA | 1020
| AAATAATATT | ATAAGAAGTA | ACATAATTGT | CAAATGAAAT | ACACATAAGA | AGCACATAAA | 1080
| TTTAAATGCC | GTATTAAACT | TACAGTATAC | TATAGCGGAA | GTTGGCTTGA | TAAAGGAACG | 1140
| CTGAGGAGAG | TAGCCGATGG | TGAAACACTA | ACATCAAGTG | CAAAAGAAAG | AAAAACTGAA | 1200
| AACAGAAGAT | GAATGTTTGA | AGTGGGTAAA | AGATTACTTA | AAAGATAGGT | TTGGTTAACA | 1260
| AATGATTGTG | ACTGTTACGA | AGCAGTGTGA | ACCGTTGGGA | CTTTTAATAT | TCTTCGGCAG | 1320
| AAGAACATTG | CTCTTTCCAC | GTATGTAGTC | TTTGTCTACT | TGTAGTTTTT | TTAATTTAA  | 1380
| ATTAAATAAG | TTAATTAGAG | AAATAATAAG | AAGGATATTT | TAGTAATTCA | ACTTTTAACT | 1440
| TTTAGGTTTC | CCACTTATAA | TATAATATAG | ATATAGTTTT | TTTAATTTA  | AATTAAATAA | 1500
| GTTAATTAGA | GAAATAATAA | GAAGGATATT | TTAGTAATTC | AACTTTTAAC | TTTTAGGGTT | 1560
| TCCACTTATA | ATATAATATA | GATATAGATA | TAGATATAGA | TATAGATAAA | GATATATAGA | 1620
| TATAGATAGA | TAATATAGAT | GGATGAGTCA | TTGGCGATAA | AGTGAGGATT | GTTTCATTTT | 1680
| TGTTATTAAA | AACTTACTAC | TCCTTAAATA | TAAATATGA  | TTCCTTTTAA | AAAAGAAATA | 1740
| GAATAAAAAT | AAAGATAAAA | CACTAAAAAT | AAATTAATTG | TCTAGACAAA | ATCTACCGTT | 1800
| CACCTCAATT | AATACACATC | CCCGTCCACA | TCATGAAGTA | GCTAGCACAA | GCGTACAGAT | 1860
| CAGTTGAAAG | AAGAAAGGG  | TCCAGTCCTA | AATATCCAAA | TGTTCATGAA | AGGAGGACAA | 1920
| CTTAGTTTTT | TCTACTAGAA | AGAATATTTT | GACGAATTTC | GTTCACATTG | GCATGCTTTA | 1980
| ATTATATTAA | GTAGTCTTTC | TTGGAAAAGA | AGTATTTGCA | ATATCAAACC | AAATCTTCCC | 2040
| ATTACGCAAG | CAATGACATC | TAAGCAAATA | TATATCACTA | TAAATAGTAC | TACTAATGTT | 2100
| CAATGACTTT | TATAAGCACT | ACATATATAT | ACTCAAACAA | AAAGAATGGA | GAGCAACAAC | 2160
| GTGGTTCTGC | TAGATTTCTG | GCCAAGCTCT | TTTGGTATGA | GGCTAAGAAT | TGCATTGGCC | 2220
| TTAAAGGGAA | TCAAATATGA | AGCAAGGAG  | GAAAACTTAT | CTGATAAAAG | CCCTTTGCTT | 2280
| CTGGAGATGA | ACCCTGTTCA | CAAAAAGATC | CCTATTTTGA | TTCACAATAG | TAAAGCCATT | 2340
| TGTGAGTCTC | TAAACATTCT | TGAGTACATT | GATGAAGTCT | GGCATGACAA | ATGTCCATTA | 2400
| CTTCCTTCTG | ATCCTTACGA | AAAGTCACAA | GCCAGATTCT | GGGCCGACTA | TATTGACAAG | 2460

| | | | | | |
|---|---|---|---|---|---|
| AAGGTAATAA | ACATCTCACA | AAGACTTAAC | AGTCAATGTA | ACATGACCTT | TACTAAGTTC | 2520
| ATCTTGTGTA | GTTTCACCGA | GCTGTTTAAG | GTCGTCGTAC | ATTTGAATAT | TAGGTGTTTC | 2580
| ACATTTGAAT | TTTTTTATCC | CCTTGTTAGA | ATTCCTGATT | CTGTCAATAC | TTATGGACGT | 2640
| TGGTTTAATG | CAGATATATA | GCACAGGAAG | AAGAGTGTGG | AGCGGTAAAG | GTGAAGATCA | 2700
| AGAAGAAGCA | AAGAAGGAAT | TCATAGAAAT | ACTCAAGACT | TTGGAAGGAG | AGCTTGGAAA | 2760
| TAAAACTTAC | TTTGGTGGTG | ATAATCTGGG | TTTTGTGGAT | GTGGCTTTGG | TTCCCTTTAC | 2820
| TAGTTGGTTT | TATTCTTATG | AGACTTGTGC | AAACTTTAGT | ATAGAAGCAG | AGTGTCCAAA | 2880
| GCTGGTGGTA | TGGGCAAAAA | CATGTATGGA | GAGCGAGAGT | GTCTCAAAGT | CCCTTCCTCA | 2940
| TCCTCACAAG | ATCTATGGTT | TTGTCTTGGA | ACTCAAGCAC | AAGCTTGGTC | TTGCTTGAAC | 3000
| AAGAAACACT | TCTTACCTAC | TGCAGAAACC | AATCATGTCC | TTCGTC | | 3046

( 2 ) INFORMATION FOR SEQ ID NO: 8:

( i ) SEQUENCE CHARACTERISTICS:
( A ) LENGTH: 809 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO: 8:

| | | | | | |
|---|---|---|---|---|---|
| ACGTATGTAG | TCTTTGTCTA | CTTGTAGTTT | TTTTTAATTT | AAATTAAATA | AGTTAATTAG | 60
| AGAAATAATA | AGAAGGATAT | TTTAGTAATT | CAACTTTTAA | CTTTTAGGTT | TCCCACTTAT | 120
| AATATAATAT | AGATATAGTT | TTTTTAATT | TAAATTAAAT | AAGTTAATTA | GAGAAATAAT | 180
| AAGAAGGATA | TTTTAGTAAT | TCAACTTTTA | ACTTTTAGGG | TTTCCACTTA | TAATATAATA | 240
| TAGATATAGA | TATAGATATA | GATATAGATA | AAGATATAT | AGATATAGAT | AGATAATATA | 300
| GATGGATGAG | TCATTGGCGA | TAAAGTGAGG | ATGTTTCATT | TTTGTTATTA | AAAACTTACT | 360
| ACTCCTTAAA | TATAAAATAT | GATTCCTTTT | AAAAAGAAA | TAGAATAAAA | ATAAAGATAA | 420
| AACACTAAAA | ATAAATTAAT | TGTCTAGACA | AAATCTACCG | TTCACCTCAA | TTAATACACA | 480
| TCCCCGTCCA | CATCATGAAG | TAGCTAGCAC | AAGCGTACAG | ATCAGTTGAA | AGAAGAAAAG | 540
| GGTCCAGTCC | TAAATATCCA | AATGTTCATG | AAAGGAGGAC | AACTTAGTTT | TTTCTACTAG | 600
| AAAGAATATT | TTGACGAATT | TCGTTCACAT | TGGCATGCTT | TAATTTATTA | AGTAGTCTTT | 660
| CTTGGAAAAG | AAGTATTTGC | AATATCAAAC | CAAATCTTCC | CATTACGCAA | GCAATGACAT | 720
| CTAAGCAAAT | ATATATCACT | ATAAATAGTA | CTACTAATGT | TCAATGACTT | TTATAAGCAC | 780
| TACATATATA | TTCTCAAACA | AAAAGAATG | | | | 809

( 2 ) INFORMATION FOR SEQ ID NO: 9:

( i ) SEQUENCE CHARACTERISTICS:
( A ) LENGTH: 331 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( x i ) SEQUENCE DESCRIPTION: SEQ ID NO: 9:

| | | | | | |
|---|---|---|---|---|---|
| ACGTATGTAG | TCTTTGTCTA | CTTGTAGTTT | TTTTTAATTT | AAATTAAATA | AGTTAATTAG | 60

-continued

| AGAAATAATA | AGAAGGATAT | TTTAGTAATT | CAACTTTTAA | CTTTTAGGTT | TCCCACTTAT | 120 |
| AATATAATAT | AGATATAGTT | TTTTTAATT | TAAATTAAAT | AAGTTAATTA | GAGAAATAAT | 180 |
| AAGAAGGATA | TTTAGTAAT | TCAACTTTTA | ACTTTTAGGG | TTTCCACTTA | TAATATAATA | 240 |
| TAGATATAGA | TATAGATATA | GATAGATA | AAAGATATAT | AGATATAGAT | AGATAATATA | 300 |
| GATGGATGAG | TCATTGGCGA | TAAAGTGAGG | A | | | 331 |

( 2 ) INFORMATION FOR SEQ ID NO: 10:

( i ) SEQUENCE CHARACTERISTICS:
        ( A ) LENGTH: 314 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO: 10:

| TGTTTCATTT | TTGTTATTAA | AAACTTACTA | CTCCTTAAAT | ATAAAATATG | ATTCCTTTTA | 60 |
| AAAAAGAAAT | AGAATAAAAA | TAAAGATAAA | ACACTAAAAA | TAAATTAATT | GTCTAGACAA | 120 |
| AATCTACCGT | TCACCTCAAT | TAATACACAT | CCCCGTCCAC | ATCATGAAGT | AGCTAGCACA | 180 |
| AGCGTACAGA | TCAGTTGAAA | GAAGAAAGG | GTCCAGTCCT | AAATATCCAA | ATGTTCATGA | 240 |
| AAGGAGGACA | ACTTAGTTTT | TTCTACTAGA | AAGAATATTT | TGACGAATTT | CGTTCACATT | 300 |
| GGCATGCTTT | AATT | | | | | 314 |

( 2 ) INFORMATION FOR SEQ ID NO: 11:

( i ) SEQUENCE CHARACTERISTICS:
        ( A ) LENGTH: 161 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO: 11:

| TATTAAGTAG | TCTTTCTTGG | AAAAGAAGTA | TTTGCAATAT | CAAACCAAAT | CTTCCCATTA | 60 |
| CGCAAGCAAT | GACATCTAAG | CAAATATATA | TCACTATAAA | TAGTACTACT | AATGTTCAAT | 120 |
| GACTTTTATA | AGCACTACAT | ATATATTCTC | AAACAAAAG | A | | 161 |

( 2 ) INFORMATION FOR SEQ ID NO: 12:

( i ) SEQUENCE CHARACTERISTICS:
        ( A ) LENGTH: 307 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO: 12:

| CTTTTAATAT | TCTTCGGCAG | AAGAACATTG | CTCTTTCCAC | GTATGTAGTC | TTTGTCTACT | 60 |
| TGTAGTTTTT | TTTAATTTAA | ATTAAATAAG | TTAATTAGAG | AAATAATAAG | AAGGATATTT | 120 |
| TAGTAATTCA | ACTTTTAACT | TTTAGGTTTC | CCACTTATAA | TATAATATAG | ATATAGTTTT | 180 |
| TTTTAATTTA | AATTAAATAA | GTTAATTAGA | GAAATAATAA | GAAGGATATT | TTAGTAATTC | 240 |

-continued

| AACTTTTAAC | TTTTAGGGTT | TCCACTTATA | ATATAATATA | GATATAGATA | TAGATATAGA | 300 |
| TATAGAT | | | | | | 307 |

(2) INFORMATION FOR SEQ ID NO: 13:

(i) SEQUENCE CHARACTERISTICS:
      (A) LENGTH: 538 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (xi) SEQUENCE DESCRIPTION: SEQ ID NO: 13:

| AAAGATATAT | AGATATAGAT | AGATAATATA | GATGGATGAG | TCATTGGCGA | TAAAGTGAGG | 60 |
| ATTGTTTCAT | TTTTGTTATT | AAAAACTTAC | TACTCCTTAA | ATATAAAATA | TGATTCCTTT | 120 |
| TAAAAAGAA | ATAGAATAAA | AATAAAGATA | AAACACTAAA | AATAAATTAA | TTGTCTAGAC | 180 |
| AAAATCTACC | GTTCACCTCA | ATTAATACAC | ATCCCCGTCC | ACATCATGAA | GTAGCTAGCA | 240 |
| CAAGCGTACA | GATCAGTTGA | AAGAAGAAAA | GGGTCCAGTC | CTAAATATCC | AAATGTTCAT | 300 |
| GAAAGGAGGA | CAACTTAGTT | TTTTCTACTA | GAAAGAATAT | TTGACGAAT | TTCGTTCACA | 360 |
| TTGGCATGCT | TTAATTATAT | TAAGTAGTCT | TTCTTGGAAA | AGAAGTATTT | GCAATATCAA | 420 |
| ACCAAATCTT | CCCATTACGC | AAGCAATGAC | ATCTAAGCAA | ATATATATCA | CTATAAATAG | 480 |
| TACTACTAAT | GTTCAATGAC | TTTTATAAGC | ACTACATATA | TATACTCAAA | CAAAAAGA | 538 |

(2) INFORMATION FOR SEQ ID NO: 14:

(i) SEQUENCE CHARACTERISTICS:
      (A) LENGTH: 4284 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (xi) SEQUENCE DESCRIPTION: SEQ ID NO: 14:

| AAGCTTGGCA | AGGCTGACCA | AAGTCACAGA | AGCGATTGGA | ATTCGCAGGA | CAGACCATGC | 60 |
| ACCTGCGCAC | AAAATGTCGT | AGGTGCGACA | CACCAGAACC | AGCACTGGGC | AGCAGGTTTC | 120 |
| AATTGCTCTG | TGGCTCGTTT | GAAACTCATC | CGAGCCACTC | ATGACCTCGT | CCGAATATTT | 180 |
| CAACAAGTCC | ATAAACATAA | TACGGACATA | CTCGGGGTTT | CACTTCACGT | CAAACAACAT | 240 |
| CAAAATTACA | AATCACACCC | CGATTCGAAC | CTTGAGTTTT | AAACTTTTCA | ATTTGCAAAT | 300 |
| CTCGTGCCAA | AACATATTAA | ATGAATCCGG | AATGACTTCA | AATTTATAAA | TGACATAACG | 360 |
| GAGTTGTTCA | AATTTCCAGA | ATCAGATTCT | GCCTTTGATA | TCAAAAAGTC | AACCCCGTGA | 420 |
| TCAAACTTGG | AATTCTTTAG | CCTTTAAATT | GCTAGTTTTC | GTTAAATGGT | CATAACTTGA | 480 |
| GCTATGGACC | TCCAAATTAA | ATTCGGGCA | TACGCTCAAA | TCCCAATTAC | GAATACGGAG | 540 |
| CTACCGGACT | GTCAAAATAC | TGATCCGGGT | CCGTTTGCTA | AAAACGTTGA | CCAAAGTCCA | 600 |
| CTAAGTTGAG | TTTTAAAACT | TTATTTCACA | TTTTAATCCA | TTTTTACAT | GAAAACTTTC | 660 |
| CGGAAAATAC | GGAGTATGCA | CGCAAGTCGA | GGAATGATAA | ATGGTACGTT | TCGAAGTTTT | 720 |
| AGAACTCAAA | ATTACTTATT | AAATTTAAAG | ATGACATTTT | GGGTCATCAC | ATTGATGAAA | 780 |
| ATTTTGACAT | TAATATCTGA | GAACTTTCTT | TGACCTTTTT | CGATTCTAAT | CCAATCAATT | 840 |

| | | | | | |
|---|---|---|---|---|---|
| CAACAGTGTA | AGGTGAAGCA | GTCAATTTAA | AGGAAGGCCT | TTAAATTCTA | AAATATTGTA | 900
| CTTTTCCTGC | GCTTCTAAAA | GTGAACGACA | AAGAAAAAAT | AGTTATTCTT | GAACTTAATA | 960
| TTGTACAATA | GGATAAATTT | TAACTATCTA | TAAAAGAGA | ACAAAACCTT | AATCTCTTCA | 1020
| AAATAATATT | ATAAGAAGTA | ACATAATTGT | CAAATGAAAT | ACACATAAGA | AGCACATAAA | 1080
| TTTAAATGCC | GTATTAAACT | TACAGTATAC | TATAGCGGAA | GTTGGCTTGA | TAAAGGAACG | 1140
| CTGAGGAGAG | TAGCCGATGG | TGAAACACTA | ACATCAAGTG | CAAAAGAAAG | AAAAACTGAA | 1200
| AACAGAAGAT | GAATGTTTGA | AGTGGGTAAA | AGATTACTTA | AAAGATAGGT | TTGGTTAACA | 1260
| AATGATTGTG | ACTGTTACGA | AGCAGTGTGA | ACCGTTGGGA | CTTTTAATAT | TCTTCGGCAG | 1320
| AAGAACATTG | CTCTTTCCAC | GTATGTAGTC | TTTGTCTACT | TGTAGTTTTT | TTTAATTTAA | 1380
| ATTAAATAAG | TTAATTAGAG | AAATAATAAG | AAGGATATTT | TAGTAATTCA | ACTTTTAACT | 1440
| TTTAGGTTTC | CCACTTATAA | TATAATATAG | ATATAGTTTT | TTTAATTTA | AATTAAATAA | 1500
| GTTAATTAGA | GAAATAATAA | GAAGGATATT | TTAGTAATTC | AACTTTTAAC | TTTTAGGGTT | 1560
| TCCACTTATA | ATATAATATA | GATATAGATA | TAGATATAGA | TATAGATAAA | GATATATAGA | 1620
| TATAGATAGA | TAATATAGAT | GGATGAGTCA | TTGGCGATAA | AGTGAGGATT | GTTTCATTTT | 1680
| TGTTATTAAA | AACTTACTAC | TCCTTAAATA | TAAAATATGA | TTCCTTTTAA | AAAAGAAATA | 1740
| GAATAAAAAT | AAAGATAAAA | CACTAAAAAT | AAATTAATTG | TCTAGACAAA | ATCTACCGTT | 1800
| CACCTCAATT | AATACACATC | CCCGTCCACA | TCATGAAGTA | GCTAGCACAA | GCGTACAGAT | 1860
| CAGTTGAAAG | AAGAAAAGGG | TCCAGTCCTA | AATATCCAAA | TGTTCATGAA | AGGAGGACAA | 1920
| CTTAGTTTTT | TCTACTAGAA | AGAATATTTT | GACGAATTTC | GTTCACATTG | GCATGCTTTA | 1980
| ATTATATTAA | GTAGTCTTTC | TTGGAAAAGA | AGTATTTGCA | ATATCAAACC | AAATCTTCCC | 2040
| ATTACGCAAG | CAATGACATC | TAAGCAAATA | TATATCACTA | TAAATAGTAC | TACTAATGTT | 2100
| CAATGACTTT | TATAAGCACT | ACATATATAT | ACTCAAACAA | AAAGAATGGA | GAGCAACAAC | 2160
| GTGGTTCTGC | TAGATTTCTG | GGGGTACGGT | CAGTCCCTTA | TGTTACGTCC | TGTAGAAACC | 2220
| CCAACCCGTG | AAATCAAAAA | ACTCGACGGC | CTGTGGGCAT | TCAGTCTGGA | TCGCGAAAAC | 2280
| TGTGGAATTG | ATCAGCGTTG | GTGGGAAAGC | GCGTTACAAG | AAAGCCGGGC | AATTGCTGTG | 2340
| CCAGGCAGTT | TTAACGATCA | GTTCGCCGAT | GCAGATATTC | GTAATTATGC | GGGCAACGTC | 2400
| TGGTATCAGC | GCGAAGTCTT | TATACCGAAA | GGTTGGGCAG | GCCAGCGTAT | CGTGCTGCGT | 2460
| TTCGATGCGG | TCACTCATTA | CGGCAAAGTG | TGGGTCAATA | ATCAGGAAGT | GATGGAGCAT | 2520
| CAGGGCGGCT | ATACGCCATT | TGAAGCCGAT | GTCACGCCGT | ATGTTATTGC | CGGGAAAAGT | 2580
| GTACGTATCA | CCGTTTGTGT | GAACAACGAA | CTGAACTGGC | AGACTATCCC | GCCGGGAATG | 2640
| GTGATTACCG | ACGAAAACGG | CAAGAAAAAG | CAGTCTTACT | TCCATGATTT | CTTTAACTAT | 2700
| GCCGGAATCC | ATCGCAGCGT | AATGCTCTAC | ACCACGCCGA | ACACCTGGGT | GGACGATATC | 2760
| ACCGTGGTGA | CGCATGTCGC | GCAAGACTGT | AACCACGCGT | CTGTTGACTG | GCAGGTGGTG | 2820
| GCCAATGGTG | ATGTCAGCGT | TGAACTGCGT | GATGCGGATC | AACAGGTGGT | TGCAACTGGA | 2880
| CAAGGCACTA | GCGGCACTTT | GCAAGTGGTG | AATCCGCACC | TCTGGCAACC | GGGTGAAGGT | 2940
| TATCTCTATG | AACTGTGCGT | CACAGCCAAA | AGCCAGACAG | AGTGTGATAT | CTACCCGCTT | 3000
| CGCGTCGGCA | TCCGGTCAGT | GGCAGTGAAG | GGCGAACAGT | TCCTGATTAA | CCACAAACCG | 3060
| TTCTACTTTA | CTGGCTTTGG | TCGTCATGAA | GATGCGGACT | TACGTGGCAA | AGGATTCGAT | 3120
| AACGTGCTGA | TGGTGCACGA | CCACGCATTA | ATGGACTGGA | TTGGGGCCAA | CTCCTACCGT | 3180
| ACCTCGCATT | ACCCTTACGC | TGAAGAGATG | CTCGACTGGG | CAGATGAACA | TGGCATCGTG | 3240

```
GTGATTGATG  AAACTGCTGC  TGTCGGCTTT  AACCTCTCTT  TAGGCATTGG  TTTCGAAGCG    3300

GGCAACAAGC  CGAAAGAACT  GTACAGCGAA  GAGGCAGTCA  ACGGCGAAAC  TCAGCAAGCG    3360

CACTTACAGG  CGATTAAAGA  GCTGATAGCG  CGTGACAAAA  ACCACCCAAG  CGTGGTGATG    3420

TGGAGTATTG  CCAACGAACC  GGATACCCGT  CCGCAAGTGC  ACGGGAATAT  TCGCCACTG     3480

GCGGAAGCAA  CGCGTAAACT  CGACCCGACG  CGTCCGATCA  CCTGCGTCAA  TGTAATGTTC    3540

TGCGACGCTC  ACACCGATAC  CATCAGCGAT  CTCTTTGATG  TGCTGTGCCT  GAACCGTTAT    3600

TACGGATGGT  ATGTCCAAAG  CGGCGATTTG  GAAACGGCAG  AGAAGGTACT  GGAAAAAGAA    3660

CTTCTGGCCT  GGCAGGAGAA  ACTGCATCAG  CCGATTATCA  TCACCGAATA  CGGCGTGGAT    3720

ACGTTAGCCG  GGCTGCACTC  AATGTACACC  GACATGTGGA  GTGAAGAGTA  TCAGTGTGCA    3780

TGGCTGGATA  TGTATCACCG  CGTCTTTGAT  CGCGTCAGCG  CCGTCGTCGG  TGAACAGGTA    3840

TGGAATTTCG  CCGATTTTGC  GACCTCGCAA  GGCATATTGC  GCGTTGGCGG  TAACAAGAAA    3900

GGGATCTTCA  CTCAGCGACC  GCAAACCGAA  GTCGGCGGCT  TTCTGCTGC   AAAAACGCTG    3960

GACTGGCATG  AACTTCGGTG  AAAAACCGCA  GCAGGGAGGC  AAACAATGAG  AGCTCGAATT    4020

TCCCCGATCG  TTCAAACATT  TGGCAATAAA  GTTTCTTAAG  ATTGAATCCT  GTTGCCGGTC    4080

TTGCGATGAT  TATCATATAA  TTTCTGTTGA  ATTACGTTAA  GCATGTAATA  ATTAACATGT    4140

AATGCATGAC  GTTATTTATG  AGATGGGTTT  TTATGATTAG  AGTCCCGCAA  TTATACATTT    4200

AATACGCGAT  AGAAAACAAA  ATATAGCGCG  CAAACTAGGA  TAAATTATCG  CGCGCGGTGT    4260

CATCTATGTT  ACTAGATCGA  ATTC                                              4284
```

( 2 ) INFORMATION FOR SEQ ID NO: 15:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO: 15:

```
ACTACTAATG  TTCAATGACT  TTTATAAGCA  CTACATATAT  ATACTCAAAC  AAAAAGAG      58
```

( 2 ) INFORMATION FOR SEQ ID NO: 16:

( i ) SEQUENCE CHARACTERISTICS:
        ( A ) LENGTH: 1863 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO: 16:

```
AAGCTTGCAC  GACACACTTG  TCTACTCCAA  AAATATCAAA  GATACAGTCC  TCAGAAGACC    60

AAAGGGCCAA  TTGAGACTTT  TCAACAAAGG  GTAATATCCG  GAAACCTCCT  CGGATTCCAT    120

TGCCCAGCTA  TCTGTCACTT  TATTGTGAAG  ATAGTGGAAA  AGGAAGGTGG  CTCCTACAAA    180

TGCCATCATT  GCGATAAAGG  AAAGGCCATC  GTTGAAGATG  CCTCTGCCGA  CAGTGGTCCC    240

AAAGATGGAC  CCCCACCCAC  GAGGAGCATC  GTGGAAAAAG  AAGACGTTCC  AACCACGTCT    300

TCAAAGCAAG  TGGATTGATG  TGATATCTCC  ACTGACGTAA  GGGATGACGC  ACAATCCCAC    360
```

```
TATCCTTCGC  AAGACCCTTC  CTCTATATAA  GGAAGTTCAT  TTCATTTGGA  GAGAACACGG   420
GGGACTCTAG  AGGATCCATG  AGGCGAACTT  CTAAATTGAC  TACTTTTTCT  TTGCTGTTTT   480
CTCTGGTTTT  GCTGAGTGCT  GCCTTGGCAC  AGAATTGTGG  TTCACAGGGC  GGAGGCAAAG   540
TTTGTGCGTC  GGGACAATGT  TGCAGCAAAT  TCGGGTGGTG  CGGTAACACT  AATGACCATT   600
GTGGTTCTGG  CAATTGTCAA  AGTCAGTGTC  CAGGTGGCGG  CCCTGGTCCT  GGTCCTGTTA   660
CTGGTGGGGA  CCTCGGAAGC  GTCATCTCAA  ATTCTATGTT  TGATCAAATG  CTTAAGCATC   720
GTAACGAAAA  TTCTTGTCAA  GGAAAGAATA  ATTTCTACAG  TTACAATGCC  TTTATTACTG   780
CTGCTAGGTC  TTTTCCTGGC  TTTGGTACAA  GTGGTGATAT  CAATGCCCGT  AAAAGGGAAA   840
TTGCTGCTTT  CTTTGCCCAA  ACCTCCCATG  AAACTACTGG  TATGTGTATA  ACCATTCACA   900
TCGAACCATT  AAAATATAAT  TTCATTTTAT  TTTATTTAGT  AATTGATTAT  ATATGTAGGA   960
GGATGGCCTT  CCGCACCTGA  TGGACCATTC  GCATGGGGTT  ACTGTTTCCT  TAGAGAACGA  1020
GGTAACCCCG  GTGACTACTG  TTCACCAAGT  AGTCAATGGC  CTTGTGCACC  TGGAAGGAAA  1080
TATTTCGGAC  GAGGCCCAAT  CCAAATTTCA  CAGTAAGCTA  CATAAATCTA  TATATGGTAA  1140
AATTTGATGA  ACTTGTAGTG  TCTAATTACG  TGTATTTTGA  CATTTCAAAA  CAGCAACTAC  1200
AACTATGGGC  CATGTGGAAG  AGCCATCGGA  GTGGACCTTT  TAAACAATCC  TGATTTAGTA  1260
GCCACAGACC  CAGTCATCTC  ATTCAAGACT  GCTATCTGGT  TCTGGATGAC  CCCTCAATCA  1320
CCAAAGCCTT  CTTGCCACGA  TGTCATCATT  GGAAGATGGA  ACCCATCTGC  CGGTGACCGA  1380
TCAGCCAATC  GTCTTCCTGG  ATTTGGTGTC  ATCACAAACA  TCATCAATGG  GGGCCTGGAA  1440
TGTGGTCGTG  GCAATGACAA  TAGGGTCCAG  GATCGCATTG  GGTTTTACAG  GAGGTATTGC  1500
GGTATTCTTG  GTGTTAGTCC  TGGTGACAAT  CTTGATTGCG  GAAACCAGAG  ATCTTTTGGA  1560
AACGGACTTT  TAGTCGATAC  TATGTAATGA  GCTCGAATTT  CCCCGATCGT  TCAAACATTT  1620
GGCAATAAAG  TTTCTTAAGA  TTGAATCCTG  TTGCCGGTCT  TGCGATGATT  ATCATATAAT  1680
TTCTGTTGAA  TTACGTTAAG  CATGTAATAA  TTAACATGTA  ATGCATGACG  TTATTTATGA  1740
GATGGGTTTT  TATGATTAGA  GTCCCGCAAT  TATACATTTA  ATACGCGATA  GAAAACAAAA  1800
TATAGCGCGC  AAACTAGGAT  AAATTATCGC  GCGCGGTGTC  ATCTATGTTA  CTAGATCGAA  1860
TTC                                                                    1863
```

( 2 ) INFORMATION FOR SEQ ID NO: 17:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO: 17:

```
GAANNGAANN TTCNNTTC                                                      18
```

( 2 ) INFORMATION FOR SEQ ID NO: 18:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

(iii) HYPOTHETICAL: NO (xi) SEQUENCE DESCRIPTION: SEQ ID NO: 18:

TTCNNTTCNN GAANNGAA    18

PLANT PROMOTER, MICROORGANISMS AND PLANT CELLS CONTAINING A UNIT FOR THE EXPRESSION OF A PROTEIN OF INTEREST COMPRISING SAID PROMOTER

The present invention relates to a novel plant promoter and to the microorganisms and plant cells containing a unit for the expression of a protein of interest comprising said promoter. The promoter according to the invention is a strong constitutive promoter enabling said protein to be expressed in microorganisms and plant cells irrespective of the stage of development of the plant.

Furthermore, the promoter according to the invention has a particular application in the field of the protection of plants by genetic engineering and especially that of the defense of plants in stress conditions.

BACKGROUND OF THE INVENTION

The applications of plant transformation have increased over recent years. Numerous genes of prokaryotic or eukaryotic (animal or vegetable) origin, coding especially for proteins which confer a novel agronomic property when expressed, have been isolated and then transferred to plants.

In a very large number of cases, the genes which have been introduced into plants by genetic engineering are chimeric, associating regulatory elements of different origins. Thus, very often, the gene coding for a protein of interest is placed under the control of a strong constitutive promoter enabling said protein to be expressed in the whole plant (or the major part thereof) throughout its life, irrespective of the stage of development. The promoter of the 35S transcript of the cauliflower mosaic virus (35S CaMV), which is the most widely used in constructions of chimeric genes, corresponds to this description.

Now, for a number of applications, it is not necessary for the gene coding for the protein of interest, supporting the agronomic property, to have a continuous expression or an expression distributed throughout the whole plant. In certain cases, such characteristics can even reduce or annul the beneficial effects of the transferred gene. In fact, the continuous expression of a protein at a high level can divert part of the metabolism towards this expression and ultimately cause a loss of yield.

Very soon, the search for et more specific gene expression was undertaken; it led for example to the isolation of tissue- or organ-specific promoters.

It can be of interest to induce the expression of a given gene only in a precise situation or, preferably, to ensure a base expression level throughout the life of a plant while at the same time allowing the superexpression of the gene in a given situation.

Several inducible promoters have already been described, some of which respond both to infection by pathogenic microorganisms and to chemical compounds or plant hormones, such as ethylene (Roby et al., 1990, Plant Cell, 2, 999) or auxin.

A plant promoter isolated from tobacco has been described by Takahashi et al., Proc. Natl. Acad. Sci. USA, 1990, 87, 8013–8016.

In another publication, these authors state that this promoter reacts specifically only to auxins and not to other hormones or to stress (Takahashi et al., The Plant Journal, 1991, 1(3), 327–332).

SUMMARY OF THE INVENTION

The present invention relates to a promoter which is expressed at a sustained level in the different organs and tissues of a plant, and especially the roots and meristem of a plant, and which is very strongly inducible in stress situations such as, in particular, after a heat shock, a wound, a hormone shock, a biotic or abiotic elicitor or a bacterial, fungal or viral infection.

The invention further relates to the microorganisms (bacteria) and plant cells which have integrated a unit for the expression of a protein of interest, said unit comprising the promoter according to the invention.

It further relates to the plants or parts of plants and the seeds which comprise the plant cells of the invention.

Finally, it further relates to the use of one of the above plants or parts of plants for selecting molecules with plant protection activity which are capable of inducing natural defense reactions in plants against the aggressions of phytopathogenic or phytophagic organisms (fungi, bacteria, viruses, insects and nematodes).

The promoter according to the invention comprises the DNA sequence (B) [SEQ ID NO: 4] or a sequence having a high degree of homology with the sequence (B).

In one variant, the promoter according to the invention contains, upstream from the sequence (B), a sequence (C) [SEQ ID NO: 5] or a sequence having a high degree of homology with the sequence (C).

Finally, in a preferred variant of the invention, the promoter of the invention contains, upstream from the sequence (B), a sequence (D) [SEQ ID NO: 6] or a sequence having a high degree of homology with the sequence (D).

Here a high degree of homology denotes a homology (ratio of the identical nucleotides to the total number of nucleotides) of at least 70%, and preferably of at least 80%, of the nucleotide sequences when they are aligned according to the maximum homology by the optimal sequence alignment method of Needleman and Wunsch, 1970; J. Mol. Biol., 48, 443–453. This method is used especially in the UWGCG software of the University of Wisconsin: Devereux et al., 1984, Nucl. Ac. Res., 12, 387–395—option GAP.

The elements necessary for the function of this promoter and for the expression of its characteristics (transactivating factors etc.) are present in other dicotyledonous or monocotyledonous plants. Their presence therefore enables this promoter to be used in numerous cultivated plants such as, in particular, tobacco, potato, tomato, maize, sunflower, barley and colza plants, or other plants such as yeasts and fungi.

Any DNA sequences coding for proteins of interest can be placed under the control of the promoter according to the invention, particularly sequences coding for proteins which make it possible to ensure the protection of a plant, for example against viral, bacterial or fungal infections and against the other stress conditions. Examples of such proteins which may be mentioned in particular are the tomato-tobacco endochitinases such as that described in EP-A-493 581, whose coding sequence is [SEQ ID NO: 16].

The promoter according to the invention was obtained by screening a tobacco gene library with the aid of a DNA probe having the sequence [SEQ ID NO: 1].

A clone corresponding to the sequence [SEQ ID NO: 1] was obtained by the differential screening of cDNA clones derived from poly(A)$^+$ mRNAs specifically synthesized during the infection of Nicotiana tabacum tobacco leaves with *Pseudomonas solanacearum* strain GMI1000. This bacterial strain is well known for causing a hypersensitivity reaction on tobacco of the Bottom Special variety. In this connections reference may be made to the work by Message et al., 1978, Proc. 4th Intl. Conf. of Plant Pathogenic Bacteria, pp. 823–833. The clone containing the sequence |SEQ ID NO: 1| will hereafter be called the "246 clone".

The 246 clone then made it possible, by the screening of a tobacco gene library, to isolate a clone, hereafter called the 246C clone |SEQ ID NO: 7|, which contains the DNA sequence (D) |SEQ ID NO: 6|, the DNA sequence (C) |SEQ ID NO: 5|, the DNA sequence (B) |SEQ ID NO: 4| and a sequence containing 2 open reading frames separated by an intron.

Following the procedure described in section 9 below, association of the promoter (sequences B+C+D) with the β-glucuronidase gene gave expression vector pSG123. The promoter consisting of the sequences B+C+D is called the 246C promoter.

Expression vector pSG123 was used to test the transient expression of the glucuronidase gene in tobacco protoplasts, said protoplasts being placed in a stress situation either by infection with *Pseudomonas solanacearum* or by treatment with an elicitor or a hormone.

Following the procedure described in section 13, expression vector pSG123 was used to prepare an expression vector stable in plant cells, namely binary vector pSG246.

This binary vector pSG246, was transferred to *Agrobacterium tumefaciens* or *Agrobacterium rhizogenes* cells, which were then used to obtain transgenic tobacco, colza and sunflower plants. Expression vector pSG123 was used for the transformation of tissues of monocotyledons (barley and maize). The behavior of these plants or tissues in stress conditions was studied.

The promoter according to the invention, comprising the sequence (B), (C) and (D), was also associated with the gene coding for tomato-tobacco chitinase. The resulting chimeric genes were used for transforming Agrobacterium cells.

The DNA sequence [SEQ ID NO: 1] can easily be synthesized by the techniques well known to those skilled in the art (L. J. MacPRIDE and H. M. CARUTHURS, Tetrahedron Letters (1983) vol. 24, 245).

A study of the transgenic plants obtained by the transformation of plants with the aid of Agrobacterium cells obtained above made it possible to demonstrate the base promoting activity of the promoter according to the invention, and the superexpression of the proteins of interest (β-glucuronidase and chitinase) in stress situations.

The results included in the illustrative part below clearly show that the promoter according to the invention has a base promoting activity which is greatly enhanced when the transgenic plants containing this promoter and a gene coding for a protein of interest are placed in stress conditions: heat shock, wound, infection with pathogens (fungi, bacteria), elicitors (biotic and abiotic).

Different deletions of plasmid pSG123, carried out in the 5' region of the promoter with the aid of restriction enzymes and/or nuclease Exo3, demonstrated the existence of vectors pSG251 and pSG33, the respective sequences of which are the sequence (B) (pSG33) |SEQ ID NO: 4| or the sequence (B) containing the sequence (C) (pSG251) [SEQ ID NO: 5] upstream.

Easy visualization of the expression of glucuronidase (Jefferson et al., 1987, Plant Molec. Biol. Reporter, 5, 387), or of its superexpression in the case of induction of the promoter of the invention, makes it possible to use plants which express this chimeric gene for the selection of inducer molecules.

Plants possess defense mechanisms against aggressions, especially parasitic aggressions (fungi, bacteria, viruses or insects); these mechanisms which depend on induction phenomena are not well known and often come into play too late to be effective. Early triggering of these mechanisms (Roby et al., 1988, Physiol. Molec. Plant Pathol., 33, 409), especially by elicitor-type compounds in cascade reactions, enables the plant to resist aggressions.

Second-generation fungicides, which are active on the plant's defenses while being inactive on the parasite, have already been marketed.

Plants which express glucuronidase under the control of the promoter of the invention, induced early and specifically in a hypersensitivity reaction to a bacterial infection, constitute a preferred tool for selecting molecules capable of inducing the expression or superexpression of defense gene.

The invention will be understood more clearly with the aid of the following description divided into sections, which comprises experimental results and a discussion thereof. Some of these sections refer to experiments performed for the purpose of carrying out the invention; others refer to Examples of the invention, which of course are given purely by way of illustration.

Most of the techniques below, which are well known to those skilled in the art, are described in detail in the work by Sambrook et al.: "Molecular Cloning: A laboratory manual" published in 1989 by Cold Spring Harbor Press in New York (2nd edition).

The biological material (strains, phages, plasmids or plants) used in the sections below is commercially available and/or is described respectively in the following documents:

| binary vector pBIN19: | BEVAN et al., 1984, Nucl. Ac. Res., 12, 8711–8721, obtained from Clontech (Palo Alto, California, USA) |
|---|---|
| vector 101.3: | JEFFERSON, 1987, Plant Molec. Biol. Reporter, 5, 387–405, obtained from Clontech |
| vector pBI221: | JEFFERSON, 1987, Plant Molec. Biol. Reporter, 5, 387–405, obtained from Clontech |
| vector pBI121: | JEFFERSON, 1987, Plant Molec. Biol. Reporter, 5, 387–405, obtained from Clontech |
| *Pseudomonas solanacearum* strain GMI1000: | MESSAGE et al., 1978, Proc. 4th Intl. Conf. of Plant Pathogenic Bacteria, pp. 823–833 |
| *Pseudomonas solanacearum* strain GMI1178: | MESSAGE et al., 1978, Proc. 4th Intl. Conf. of Plant Pathogenic Bacteria, pp. 823–833 |
| *Pseudomonas solanacearum* strain K60: | MESSAGE et al., 1978, Proc. 4th Intl. Conf. of Plant Pathogenic Bacteria, pp. 823–833 |
| NOS terminator: | nopaline synthase terminator |
| vector pTZ19R: | obtained from Pharmacia |
| *E. coli* strain MC1061: | MANIATIS et al., 1982, Molecular Cloning: A laboratory manual, Cold Spring Harbor, New York, obtained from Clontech |
| *E. coli* strain HB101: | MANIATIS et al., 1982, Molecular Cloning: A laboratory manual, Cold Spring Harbor, New York, obtained from Clontech |
| *Agrobacterium tumefaciens* strain: | LBA4404, obtained from Clontech, HOEKEMA et al., 1983, NATURE, 303, 179–180 |

-continued

| | |
|---|---|
| Agrobacterium rhizogenes strain: | pRIA₄ |
| Nicotiana tabacum plant: | Wisconsin Havana 38 variety: SCHNEIDER M., 1990, Plant Molec. Biol., 14, 935–947 |
| Chalara elegans fungus: | RAWLINGS R. E., 1940, Ann. Mo. Bot. Gdn., 27, 561–598 |
| Alternaria brassicae fungus: | BAINS and TEWARI, 1987, Physiol. Mol. Plant Pathol., 30, 259 |
| Nicotiana tabacum plant: | Paraguay 49 variety, obtained from the Institut du tabac, Bergerac, France |
| Brassica napus plant: | Brutor and Westar spring varieties and winter line (selection line, Rustica Semences) |
| Rhizoctonia solani pathogen: | ACHARYA et al., 1984, Can. J. Plant Pathol., 6, 325–328 |
| sunflower plants: | genotype 2603B (selection line, Rustica Semences) |
| maize: | line LH132 |
| barley: | GERBEL variety, obtained from the Institut National de la Recherche Agronomique (INRA), Paris, France |

Strains GMI1000 and K60 can be obtained from the Collection Nationale des Bactéries Phytopathogenes (CNBP) INRA, Pathologie Végétale, Rue Georges MOREL, 49070 BEAUCOUZE, FRANCE.

Strain GMI1178 can be obtained from INRA, Pathologie Végétale, Chemin de Borde-Rouge, AUZEVILLE BP 27, 31326 CASTANET TOLOSAN Cédex, FRANCE.

The following abbreviations are used in the Examples below:

32P-dCTP: deoxycytidine 5'-$^{32}$P-triphosphate marketed by AMERSHAM under the reference 10205;

2 SSC: NaCl 0.3M, trisodium citrate 30 mM; pH 7.0 (described by MANIATIS et al., op. cit.);

SDS: sodium dodecylsulfate;

FPLC: fast protein liquid chromatography;

PVDF: polyvinylidene difluoride;

EDTA: ethylenediaminetetraacetic acid;

DEPC: diethyl pyrocarbonate;

NAD: nicotinamide adenine dinucleotide.

BRIEF DESCRIPTION OF THE DRAWINGS

FIG. 2A–2B represent the alignment, according to the optimal alignment method of Needleman and Wunsch, 1970, J. Mol. Biol., 48, 443–453, applied by the UWGCG software of the University of Wisconsin (Devereux et al., 1984, Nucl. Ac. Res., 12, 387–395), option GAP, of the 3' part of 700 bp of the promoter of the 246C gene and the promoter described by Takahashi et al., 1989, Proc. Natl. Acad. Sci. USA, 87, 8013.

FIG. 3 represents the different expression vectors tested in which, relative to full-length plasmid pSG123, there is a variable deletion of the 5' part of the promoter.

DETAILED DESCRIPTION OF THE INVENTION

Figure 1:
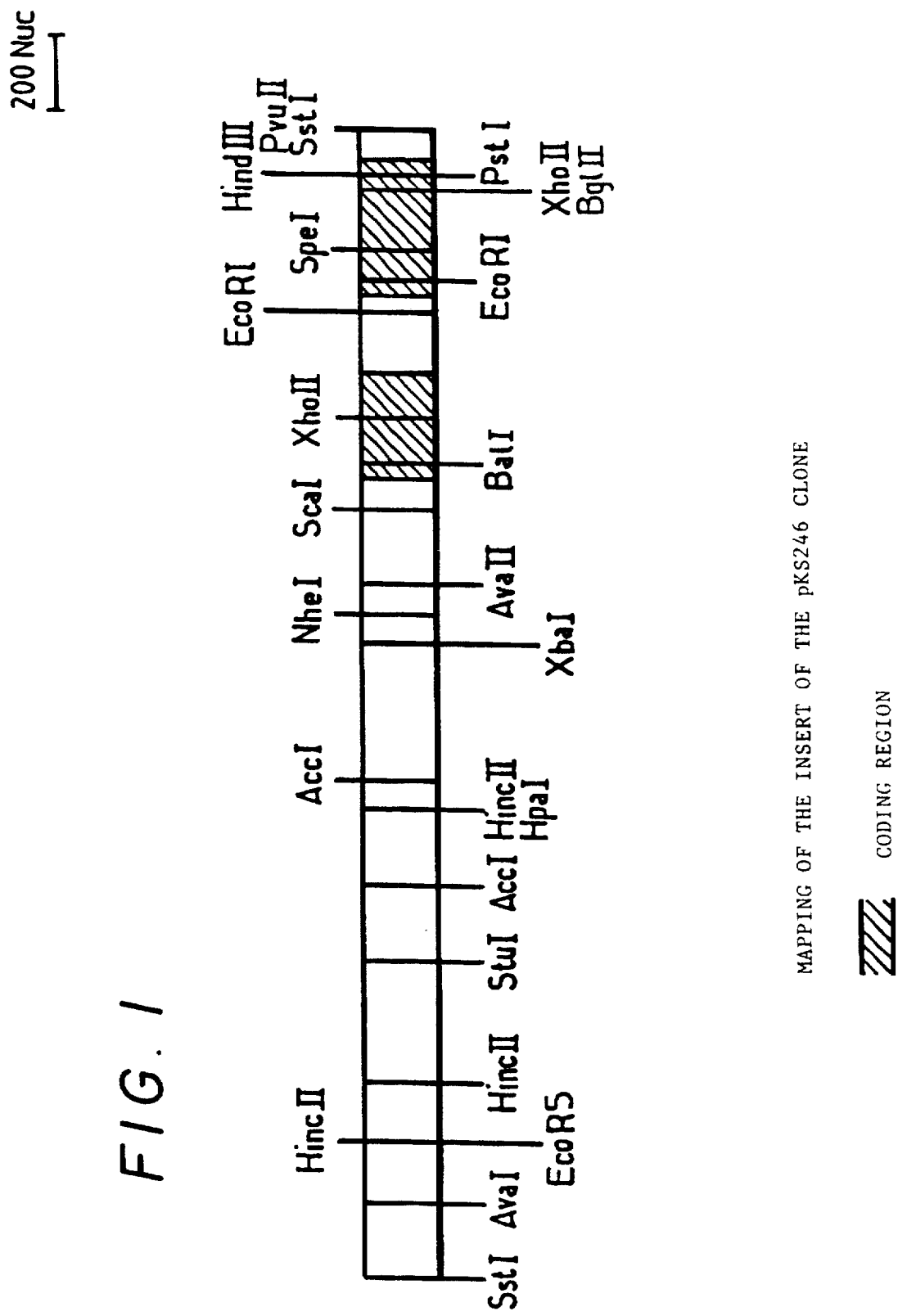
FIG. 1 represents the mapping of the 246C genomic DNA clone, established with the aid of the restriction enzymes shown.

Section 1: Infection of tobacco, Nicotiana tabacum, with two strains of the pathogenic bacterium Pseudomonas solanacearum The bacteria of the Pseudomonas solanacearum strain are cultivated for 72 h on BG agar medium (Boucher et al., 1985, J. Gen. Microbiol., 131, 2449); a colony is taken for inoculating 40 ml of the same medium. After 16 to 24 h of incubation at 28° C., the bacterial suspension is centrifuged for 10 min at 6000 g and 4° C.; the supernatant is discarded to leave the polysaccharide layer present on the surface of the residue. After washing with sterile water, the bacteria are resuspended in 20 ml of water. Their concentration is then determined by densitometry.

Young tobacco plant leaves are detached from the plant, washed with distilled water and immersed in a desiccator containing 1.2 of bacterial suspension at a concentration of $3\times10^6$ bacteria/ml. A vacuum is created for 10 min by means of a vacuum pump and is then let down slowly. Each infiltrated leaf is then placed in a beaker containing 10 mM sodium phosphate buffer of pH 6.0, and transferred to a culture chamber. The leaves are removed after different incubation times and stored at −70° C.

Two bacterial strains were used, namely strain GMI1000, which causes a hypersensitivity reaction on tobacco of the Bottom Special variety, and strain GMI1178 (Message et al., 1978, Proc. 4th Intl. Conf. of Plant Pathogenic Bacteria, pp. 823–833), a mutant which is derived from the previous strain and has lost the capacity to induce the hypersensitivity reaction in tobacco.

Section 2: Extraction and isolation of the total RNAs from *Nicotiana tabacum* infected with *Pseudomonas solanacearum* strains 10 g of plant material are ground in the presence of liquid nitrogen and then taken up in a mixture of 3 ml of phenol, 3 ml of chloroform/isoamyl alcohol (24:1, v:v) and 6 ml of the lysis buffer of composition Tris-HCl 200 mM pH 7.0, EDTA 200 mM, SDS 1%.

After agitation on a Vortex, the phases can be separated by centrifugation for 10 min at 6000 g and 4° C. The aqueous phase is removed and re-extracted with 6 ml of a phenol/chloroform/isoamyl alcohol mixture (25:24:1, v:v) and then with 6 ml of phenol. 16 ml of absolute ethanol and 400 µl of 3M sodium acetate of pH 5.5 are added to the aqueous phase; the mixture is precipitated for 2 h at −20° C. The residue obtained is dissolved in 5 ml of sterile water containing 0.1% of diethyl pyrocarbonate (DEPC), after which the RNAs are precipitated for 12 h at 4° C. following the addition of 5 ml of 4M LiCl. After centrifugation for 20 min at 6000 g, the residue of RNA is washed with 75% ethanol, dried and taken up in 800 µl of sterile distilled water containing 0.1% of DEPC. The solution is precipitated for 2 h at −20° C. following the addition of 0.1 vol of 3M sodium acetate of pH 5.5 and 2.5 vol of absolute ethanol. After centrifugation for 15 min at 12,000 g, the residue of RNA is washed with 75% ethanol and dissolved in 200 µl of distilled water containing 0.1% of DEPC.

The total RNAs are then determined by spectrophotometry at 260 nm.

Section 3: Preparation of the poly(A)$^-$ messenger RNAs 1 g of oligo d(T) cellulose gel (Collaborative Research Inc.) is resuspended in 2 ml of the buffer Tris-HCl 10 mM pH 7.4, EDTA 1 mM, NaCl 0.4M, SDS 0.1%. This gel is introduced into a Pasteur pipette whose end is plugged with glass wool. The RNA solution is heated at 65° C. for 4 min and then left to cool slowly to room temperature. A final NaCl concentration of 0.4M is obtained by adding a 5M NaCl solution.

The solution of total RNAs is then deposited on the oligo d(T) cellulose gel. This is then rinsed with about 12 ml of the buffer of composition Tris-HCl 10 mM pH 7.4, NaCl 0.4M, EDTA 1 mM, SDS 0.5%.

The poly(A)⁺ RNAs are subsequently eluted with 7 ml of the buffer of composition Tris-HCl 10 mM pH 7.4, SDS 0.1%, and then precipitated overnight at −20° C. following the addition of 2.5 volumes of 95% ethanol and 0.1 volume of 3.3M sodium acetate of pH 5.5. The residue of poly(A)⁺ RNAs obtained by centrifugation at 35,000 g for 1 h is washed 3 times with 75% ethanol, dried, taken up in 0.5 ml of sterile distilled water and reprecipitated under the conditions described above. After centrifugation, the residue is then washed with 75% ethanol, dried and dissolved in sterile distilled water. The poly(A)⁺ RNAs are then determined by spectrophotometry at 260 nm.

Section 4: Synthesis of double-stranded DNA from poly(A)⁺ messenger RNAs isolated from leaves of tobacco infected with *Pseudomonas solanacearum* strain GMI1000, and cloning into *E. coli*

This synthesis is effected by the method of Gubler and Hoffman (1983, Gene, 25, 263) using the D. Scribe kit from Genofit (Geneva, Switzerland) in accordance with the manufacturer's instructions.

Synthesis of the first strand:

2.5 μg of poly(A)$^+$ RNAs isolated from tobacco leaves infected with *Pseudomonas solanacearum* strain GMI1000 and removed 6 h after inoculation are incubated at 44° C. for 30 to 60 min in the presence of Tris-HCl 40 mM pH 8.3, NaCl 80 mM, $MgCl_2$ 6 nM, DTT 5 mM, dATP 0.5 mM, dTTP 0.5 mM, dGTP 0.5 mM, dCTP 0.5 mM, 1.5 μg of oligo d(pT) 12–18 and 10 to 15 units of AMV (avian myeloblastosis virus) reverse transcriptase in a total volume of 25 μl.

Synthesis of the second strand:

The reaction medium derived from the synthesis of the first strand is diluted to 100 μl with the buffer of composition Tris-HCl 40 mM pH 7.5, $MgCl_2$ 10 mM, NaCl 80 mM; 2 units of RNase H are added and the mixture is incubated at 37° C. for 5 min.

After cooling to 12° C., 25 units of DNA polymerase I, 0.5 Weiss unit of *E. coli* ligase and NAD in a final concentration of 0.1 mM are added.

After incubation for 60 min at 12° C. and then 60 min at 18° C., the reaction is stopped by the addition of EDTA and SDS in final concentrations of 20 mM and 1% respectively, followed by heating for 2 min at 60° C.

Purification of the cDNA:

This purification is effected by chromatography on a Sephadex G100 column in the buffer Tris-HCl 50 mM pH 7.5, NaCl 300 mM, EDTA 1 mM. The addition of alpha32P-dCTP in the synthesis step affords easier identification of the chromatographic fractions containing the double-stranded DNA. The latter is precipitated by the addition of ammonium acetate (final concentration 0.3M) and 2.5 vol of absolute ethanol.

Digestion with nuclease S1:

The precipitate obtained is washed with 75% ethanol, dried and taken up in sterile water. The cDNA is then treated with nuclease S1 in a total volume of 300 μl, at 30° C. for 10 min, in the presence of 20 U of enzyme in the buffer of composition sodium acetate 30 mM pH 4.4, NaCl 0.25M, $ZnCl_2$ 1 mM.

When the reaction has ended, the mixture is extracted once with a phenol/chloroform/isoamyl alcohol mixture (50:48:2, v:v) and then three times with ethyl ether before being precipitated with ethanol.

The DNA precipitate obtained after centrifugation is then dried and taken up in 20 μl of sterile water.

Addition of a poly dC tail at the 3' end (dC tailing):

The following are added successively to the cDNA solution: 10 μl of the terminal transferase buffer of composition potassium cacodylate 70 mM pH 7.2, $CoCl_2$ 0.5 mM, dithiothreitol 0.5 mM, 2 μl of 0.25 mM α-dCTP, 5 μl of α-32P-dCTP (370MBq/ml), 12 μl of $H_2O$ and 1.2 μl of terminal transferase (18 units).

The tailing reaction is performed by incubation at 37° C. for 30 min and is then stopped by the addition of 30 μl of 0.25M EDTA of pH 8.0.

Purification of the double-stranded cDNAs after tailing:

The mixture derived from dC tailing is precipitated with ethanol and then centrifuged. The cDNA residue is taken up in 10 μl of the buffer of composition Tris-HCl 10 mM pH 7.5, NaCl 100 mM, EDTA 1 mM, 5% glycerol, 0.02% bromophenol blue. This solution is deposited on a Biogel A 0.5M column (1 ml of support). The column is eluted with the buffer of composition Tris-HCl 10 mM pH 7.5, NaCl 100 mM, EDTA 1 mM; fractions are collected, their radioactivity is measured and the size of the cDNAs they contain is analyzed by agarose gel electrophoresis. The fractions containing cDNAs with a size of more than 500 base pairs are combined and the cDNA is precipitated with ethanol.

Hybridization with pBR322-dG:

The cDNA collected after precipitation is redissolved in 50 μl of the annealing buffer of composition Tris-HCl 20 mM pH 7.5, NaCl 100 mM, EDTA 1 mM. 4 μl of pBR322-dG solution (21 ng, Clontech) and 46 μl of water are added.

After incubation for 15 min at 65° C. and then 2 h at 57° C., the hybridization is checked by agarose gel electrophoresis.

The double-stranded cDNA obtained is inserted at the PstI site of plasmid pBR322. After ligation, the DNA obtained is used to transform competent cells of *E. coli* strain HB101. Colonies of recombinant bacteria are obtained after the transformed competent cells have been plated out and cultured on a Petri dish.

Section 5: Selection, by differential screening, of cDNA clones derived from poly(A)$^+$ mRNAs specifically synthesized during bacterial infection with *Pseudomonas solanacearum* strain GMI1000

The DNA of the recombinant bacterial colonies obtained by cloning cDNA synthesized from poly(A)$^+$ messenger RNAs of tobacco leaves infected with strain GMI1000 was transferred to a Biodyne nylon membrane (Pall Corporation, USA) in accordance with the manufacturer's instructions. These DNAs are hybridized successively with the aid of 2 radioactive probes obtained by the synthesis of cDNA, in the presence of alpha-32P-dCTP, from messenger RNAs purified from plants infected with strains GMI1000 and GMI1178 respectively.

After washing and autoradiographic exposure of the membranes, the bacterial colonies which exhibit a stronger hybridization signal with the probe synthesized from leaves inoculated with strain GMI1000 are selected. The plasmid DNA of these colonies is prepared and the cDNA inserts of these plasmids are isolated and then labeled with alpha-32P-dCTP and used as a probe for revealing, by the dot-blot and then Northern blotting technique, the equivalent amounts of corresponding mRNA purified from total RNA of tobacco leaves inoculated with strain GMI1000or GMI1178.

The colonies whose insert, used as a probe, gives a more intense signal during the revealing of the total RNAs purified from tobacco leaves inoculated with strain GMI1000 are retained.

Section 6: Characterization of a cDNA clone derived from an mRNA specifically synthesized during bacterial infection with *Pseudomonas solanacearum* strain GMI1000

14 bacterial clones were isolated from the cDNA library constructed from messenger RNAs of tobacco leaves infected with *Pseudomonas solanacearum* strain GMI1000.

One of said clones, called 246, with an insert length of 750 base pairs, enables a transcript of about 800 nucleotides to be revealed by Northern blotting. The accumulation of this transcript starts 4 to 9 h after inoculation and reaches a maximum between 12 and 15 h. In the tobacco leaves infected with strain GMI1178, a slight accumulation of the transcript is observed between 12 and 15 h.

A study of the sequence of the cDNA of the 246 clone [SEQ ID NO: 1] demonstrates the existence of a first, incomplete open reading frame coding for a peptide of 59 amino acids, and a second, potential reading frame coding for a peptide of 88 amino acids. The sequence of these two peptides is represented by [SEQ ID NO: 2]. Intron splicing consensus sequences (Brown, 1986, Nucl. Ac. Res., 14, 9549) are present between these two reading frames. Cloning of a cDNA from an immature messenger RNA has therefore probably taken place. The cDNA sequence of the 246 clone without the intron is the sequence $A_1$ [SEQ ID NO: 3].

Section 7: Screening of a tobacco gene library with the aid of the characterized cDNA A tobacco DNA gene library was obtained by partial digestion, with the enzyme MboI, of DNA isolated from the germination of *Nicotiana tabacum*, NK326 variety, and cloning of the restriction fragments into phage EMBL-3 (Clontech). 500,000 recombinant phages were screened after plating at a rate of 10,000 phages per Petri dish by the technique known to those skilled in the art and described in Sambrook et al. (Molecular Cloning, A laboratory manual, Cold Spring Harbor Laboratory Press, 1989).

The phage DNA is transferred to a nitrocellulose membrane (BA85, Schleicher and Schull), denatured for 2 min in the solution NaOH 0.5M, NaCl 1.5M and then soaked in the neutralizing solution NaCl 1.5M, Tris-HCl 0.5M pH 7.4 for 5 min. After rapid rinsing in 2 SSC (NaCl 0.3M, sodium citrate 30 mM), the filters are dried for 30 min at 37° C. and the DNA is then fixed by treatment at 80° C. under vacuum for 1 h 30 min.

The membranes are then prehybridized for 4 h at 37° C. in the buffer of composition 5 SSC (NaCl 0.75M, sodium citrate 75 mM), 50% formamide, 0.3% skimmed milk.

The hybridization is carried out in the same buffer for 18 h at 37° C. after addition of the probe labeled with alpha-32P-dCTP, which consists of the insert of 750 base pairs of the 246 cDNA clone.

The membranes are then washed 3 times for 20 min at 37° C. in the solution 5 SSC, SDS 0.1%, then twice for 30 min at 37° C. in the solution 2 SSC, SDS 0.1% and finally for 30 min at 42° C. in the solution 2 SSC, SDS 0.1%; they are then autoradiographed.

After developing of the autoradiograms, each lysis plate exhibiting a positive signal is isolated and the phages are eluted in SM medium (NaCl 100 mM, Tris-HCl 50 mM pH 7.5, $MgSO_4$ 5 mM, gelatin 0.01%) and then purified by a further screening effected under the same conditions.

12 clones were thus isolated and purified. The DNA of each clone was produced and purified by the technique well known to those skilled in the art, and then digested with the enzyme SalI, which enables the genomic DNA insert to be isolated after agarose gel electrophoresis.

Transfer to a nylon membrane, followed by hybridization with the probe consisting of the cDNA of the 246 clone, shows a positive signal, confirming the presence of a sequence complementary to the 246 cDNA in this genomic DNA.

These clones were then mapped using a series of restriction enzymes. One clone, which exhibits a hybridization signal in the central region of the fragment inserted into phage DNA, was selected from said clones. This clone was called 246C.

Section 8: Sequencing and analysis of the sequence of the 246C genomic DNA clone A fragment of the insert contained in this phage was isolated by digestion with the enzyme SstI and then cloned into phage pBluescript® 11 KS +/− (Stratagéne) to give phagemid pKS246. Its mapping was established and is shown in FIG. 1. The sequence of this insert [SEQ ID NO: 7] was then determined by the method of Sanger et al. (PNAS-US. A, 14, 5463, 1977) after the creation of progressive deletions with the aid of the enzymes ExoIII, mung bean and nuclease S1 by Henikoff's technique (Gene, 28, 351, 1984).

This insert of 3046 base pairs, called the 246C gene, consists of a coding region of 853 bp starting with an ATG in position 2146 and terminating with a TGA codon in position 2998; this region is interrupted by an intron starting in position 2464 and terminating in position 2653. Three potential transcription initiation sites were determined by primer extension using the technique described in Sambrook et al. (op. cit., 1989); the most probable site is in position 2068.

The promoter region of the 246C gene upstream from position 2146 is called the 246C promoter. A study of the sequence of the 246C promoter shows the presence of several elements known to be involved in gene regulation.

Two consensus sequences CAAT corresponding to this element for regulating the transcription of eukaryotic genes, and a complementary and inverted sequence ATTG, are present in positions 2051, 2101 and 1967.

Two consensus sequences TATAA are present in positions 2089 and 2111 and a complementary sequence AATAT in position 2020. These three elements are all located between 10 and 50 base pairs downstream from the elements CAAT and 30 to 50 base pairs upstream from the potential transcription sites.

A sequence TGACG was identified in position 1950; this sequence, whose existence is demonstrated in the 35S promoter of CaMV, seems to be responsible for the expression of chimeric genes in the roots and leaves (LAM et al., 1989, Proc. Natl. Acad. Sci. USA, 86, 7890).

Three regions exhibit a considerable homogeneity with the HSEs (heat shock elements) of plants (GURLEY and KEY, 1991, Biochemistry, 30, 1). These regions are homologous with the consensus sequence GAANNGAANNT-TCNNTTC or TTCNNTTCNNGAANNGAA; they are close to the TATA and CAAT boxes and duplicated [SEQ ID NO: 17 and NO: 18].

A sequence homologous with the element CCGTCC characterized as being involved in the response to elicitors of fungal origin (LOIS et: al., 1989, EMBO J., 8, 1641) was located in position 1822.

Over about 30% of its length, the promoter of the 246C gene has a high homology (>90%) over 700 base pairs with the plant promoter isolated from tobacco, having the sequence [SEQ ID NO: 8], described by TAKAHASHI et al., 1990, Proc. Natl. Acad. Sci. USA, vol. 87, pp. 8013–8016. FIG. 2 represents the alignment of the DNA sequence of this promoter [SEQ ID NO: 9, 10 and 11] (top line) with the corresponding part of the DNA sequence of the promoter of the invention [SEQ ID NO: 12 and 13] (bottom line).

Section 9: Construction of expression vector pSG123 associating the promoter of the 246C gene with the β-glucuronidase gene Starting from phasmid pKS246, digestion with the enzymes HindIII and BalI makes it possible to isolate an insert of about 2200 base pairs containing the promoter part of the 246C gene, the translation initiation codon and 11 codons coding for the aminoterminal part of the protein.

Plasmid pBI101.3 (Clontech) is digested with the enzymes HindIII and EcoRI; the fragment of about 2100 base pairs containing the gene of β-glucuronidase coded by the uidA locus of *E. coli*, followed by the nopaline synthase terminator of *Agrobacterium tumefaciens*, is ligated to plasmid pUC19, opened at the same sites, to give a plasmid called pBI201.3.

The HindIII-BalI insert carrying the promoter sequences of the 246C gene is cloned into plasmid pBI201.3, opened at the HindIII and SmaI sites.

The vector obtained, called pSG123, therefore contains the glucuronidase gene under the control of the promoter of the 246C gene. The nucleotide sequence of the complete chimeric gene is the sequence [SEQ ID NO: 14].

Section 10: Protocol of the transient expression of the glucuronidase gene under the control of the promoter of the 246C gene in tobacco protoplasts Preparation of tobacco protoplasts Leaves of 4- to 5-week-old tobacco plants (*Nicotiana tabacum*, var. Samsun NN) are removed, cut into thin strips and incubated in medium T0 (Table 1, adapted from Chupeau et al., 1974, C. R. Acad. Sci. (Paris), 278 D, 1565) containing 1 g/liter of Onozuka cellulase R100, 200 mg/l of Onozuka macerozyme (Yakult Honsha, Nishinoniya, Japan) and 500 mg/l of pectolyase Y23 (Sheishin Pharmaceutical Ind., Japan), for 15 h at 22° C.

The protoplasts are separated from the cellular debris by sieving on a nylon sieve of 85 μm mesh, followed by centrifugation for 5 min at 50 g on a 19% (weight/volume) sucrose solution. The protoplasts floating on this medium are washed once in medium T0 and counted and their number is adjusted to a density of 1.5×106 protoplasts/ml.

Preparation of vector pSG123

The *E. coli* strain containing vector pSG123 is cultivated on Luria medium (Gibco) containing 50 mg/l of ampicillin. The plasmid is amplified according to the protocol described in Sambrook et al., 1989 (op. cit. ). Plasmid pSG123 is then purified by centrifugation on a cesium chloride gradient and by two successive precipitations with ethanol. The plasmid residue is then redissolved in 10 mM Tris-HCl buffer of pH 8.0.

Transformation with polyethylene glycol

The protoplast suspensions (320 μl per aliquot) are incubated at 45° C. for 5 min and then rapidly cooled on ice. 50 μg of plasmid pSG123 and 160 μl of a polyethylene glycol solution (40% polyethylene glycol, 0.4M mannitol, 30 mM MgCl₂, 0.1% Mes pH 5.8) are then added. After 10 min, the protoplasts are collected by centrifugation, resuspended by gentle agitation in 500 μl of buffer T0 and incubated in the dark at 28° C.

Measurement of the transient expression

After 24 h of incubation, 50 μl of β-glucuronidase 10× extraction buffer are added and the protoplasts are then lyzed by freezing at −80° C. followed by thawing at 37° C. (Jefferson, 1987, Plant Molec. Biol. Reporter, 5, 387).

The supernatant obtained after centrifugation at 10,000 g is used to measure the β-glucuronidase activity by fluorimetry (Jefferson, , 1987, Plant Molec. Biol. Reporter, 5, 387).

In parallel, the amount of proteins present in the extracts is measured by Bradford's method using the Bio Rad kit (Bio Rad Lab.).

TABLE 1

| Composition of medium T0 (per liter) | |
| --- | --- |
| NH₄NO₃ | 825 mg |
| KNO₃ | 950 mg |
| CaCl₂.2H₂O | 220 mg |
| MgSO₄.7H₂O | 185 mg |
| KH₂PO₄ | 85 mg |
| H₃BO₃ | 1 mg |
| MnSO₄.4H₂O | 100 μg |
| ZnSO₄.7H₂O | 1 mg |
| KI | 100 μg |
| AlCl₃ | 30 μg |
| NiCl₂.6H₂O | 30 μg |
| CuSO₄.5H₂O | 30 μg |
| FeSO₄. 7H₂O | 27.8 mg |
| Na₂EDTA.2H₂O | 37.2 mg |
| Thiamine | 100 μg |
| Nicotinic acid | 200 μg |
| Pyridoxine | 1 mg |
| Biotin | 10 μg |
| Ca pantothenate | 1 mg |
| Sucrose | 20 g |
| Inositol | 100 mg |
| Mannitol | 80 g |
| 2-[N-Morpholino]ethanesulfonic acid (MES) | 200 mg | pH adjusted to 5.8 before autoclaving

Section 11: Transient expression of the glucuronidase gene under the control of the promoter of the 246C gene in tobacco protoplasts infected with *Pseudomonas solanacearum*

This transient expression, determined according to the protocol of section 10, is measured after incubation for 24 h of the protoplasts prepared according to the above protocol in medium T0 (described in section 10) containing a suspension of *Pseudomonas solanacearum* bacteria (10 bacteria/protoplast) obtained as described in section 1.

The β-glucuronidase activity is expressed in pmol of methylumbelliferone formed/min/mg of protein.

No activity is detected in the protoplasts of plants which have not received DNA of vector pSG123. An activity of 450 pmol/min/mg of protein is measured on protoplasts treated with vector pBI221 (Clontech) containing the β-glucuronidase gene under the control of the 35S constitutive promoter of CaMV; this activity is reduced to 300 pmol/min/mg of protein after infection with *Pseudomonas solanacearum* strains GMI1000 and GMI1178.

An activity of 600 pmol/min/mg of protein is measured on protoplasts treated with plasmid pSG123; this activity is largely unmodified after inoculation with strain GMI1178; it increases to a value of 1000 pmol/min/mg of protein after inoculation with strain GMI1000.

The promoter of the 246C gene therefore permits a substantial base expression of the glucuronidase gene, said expression being more substantial than that governed by the 35S promoter of CaMV, which is used here as the control. This promoter further exhibits a strong inducibility since the expression of β-glucuronidase increases by 40% after infection with bacterial strain GMI1000.

Section 12: Transient expression of the glucuronidase gene under the control of the promoter of the 246C gene of tobacco protoplasts treated with an elicitor (chitin heptasaccharides) or a hormone The expression is measured after incubation of the protoplasts for 24 h as described above in medium T0 containing an elicitor at a concentration of 25 μM or a hormone, namely 2,4-D (2,4-dichlorophenoxyacetic acid), at a concentration of 4 μM. The elicitors used (glycosidic compounds derived from the wall of pathogenic fungi) are chitin heptasaccharides with the property of inducing defense reactions in plants (Roby et al., 1987, BBRC, 143, 885).

No activity is detected in untreated protoplasts used as the control. An activity of the order of 400 pmol of methylumbellifercone formed/min/mg of protein is measured on protoplasts which have received DNA of vector pBI221; this activity is not affected by the treatment (elicitors or hormone).

Protoplasts which have received DNA of vector pSG123 have an activity of 450 pmol/min/mg of protein; this activity is increased by 50% if the protoplasts are treated with the hormone 2,4-D and by 70% if the protoplasts are treated with chitin heptasaccharide.

The characteristics of this promoter which are demonstrated when protoplasts are infected with bacterial strain GMI1000 (high base level and inducibility) can be reproduced using an inducer derived from the wall of phytopathogenic fungi.

Section 13: Construction of an expression vector stable in plant cells: binary vector pSG246

Cleavage of vector pSG123 with the restriction endonucleases HindIII and EcoRI, followed by agarose gel electrophoresis, makes it possible to isolate the chimeric gene associating the 246C promoter with the coding part of β-glucuronidase and the NOS terminator. The chimeric gene is introduced into and ligated to binary vector pBIN19 (Clontech), previously opened at the HindIII and EcoRI sites, to give vector pSG246. This binary vector possesses two kanamycin resistance genes, the one being capable of expression in bacteria and the other, located immediately upstream from the complete recombinant gene (Bevan, 1984, Nucl. Ac. Res., 12, 8711), being capable of transfer to plant cells. The kanamycin resistance gene will serve as a selectable marker during the steps involving transformation and analysis of the lineage of the transformed plants.

The vector obtained, called pSG246, is cloned into *E. coli* strain DH5α.

Section 14: Transfer to Agrobacterium of plasmid pSG246 containing β-glucuronidase under the control of the promoter of the tobacco 246C gene a) Transfer to *Agrobacterium tumefaciens*

This transfer is effected by transformation using the freeze-thaw method described in Plant Molecular Biology Manual (Gelvin et al., eds., Kluwer Academic Publishers, 1988) and is summarized below.

Competent cells of *Agrobacterium tumefaciens* (strain LBA4404, Clontech) are prepared by the rapid ice-cooling of a culture in the exponential growth phase. The bacteria are then resuspended in 20 mM $CaCl_2$. Aliquots of this suspension are distributed into Eppendorf tubes and then frozen in liquid nitrogen.

1 μg of plasmid pSG246 is added to the frozen cells contained in an Eppendorf tube. The suspension is then incubated at 37° C. for 5 min; 1 ml of Luria medium (Gibco) is then added and the tube is incubated at 28° C. for 4 h. Aliquots are plated out on Petri dishes containing a minimum agar medium described in Plant Molecular Biology Manual (op. cit.), in the presence of 100 mg of rifampicin and 25 mg/l of kanamycin. Under these conditions, only the *Agrobacterium tumefaciens* colonies which have integrated plasmid pSG246 grow. Said colonies contain the chimeric gene in a context which allows its replication.

The resistance of the selected colonies to the two antibiotics is verified by subculturing said colonies on the same selection medium twice in succession. The presence of the chimeric gene associating, the 246C promoter with the coding part of β-glucuronidase in *Agrobacterium tumefaciens* is verified by the Southern blotting method on a total DNA preparation (lysis of the cells, purification of the DNA by extraction with a phenol/chloroform mixture according to the protocol described by Gelvin in the work cited above, cleavage of the purified DNA with restriction enzymes, agarose gel electrophoresis, membrane transfer and hybridization by the techniques well known to those skilled in the art).

b) Transfer to *Agrobacterium rhizogenes*

This transfer is effected in the same manner as the transfer to *Agrobacterium tumefaciens* described in a), with *Agrobacterium rhizogenes* strain A4 described by Guerche et al., (1987) Mol. Gen. Genet., 206, 382.

Section 15: Production of tobacco plants transformed with *Agrobacterium tumefaciens* containing plasmid pSG246

Tobacco, *Nicotiana tabacum*, cultivated in vitro, was infected with *Agrobacterium tumefaciens* containing plasmid pSG246 according to the procedure of Horsch et al., which is well known to those skilled in the art (Horsch R. B. et al., 1985, Science, 227, 1229–1231) and the principal steps of which are described below.

Leaf disks from axenic tobacco plants, *Nicotiana tabacum* (Bottom Special variety), are incubated in a culture of *A. tumefaciens* containing plasmid pSG246. The disks, drained on Whatman paper, are transferred to culture media in Petri dishes for multiplication of the transformed cells to give calli (Murashige and Skoog, 1962, Physiol. Plant, 15, 473) and then to produce buds in the presence of cefotaxim (500 μg/ml), which is intended to eliminate *Agrobacterium tumefaciens*, and in the presence of kanamycin (100 μg/ml).

In parallel, transformations were carried out with *Agrobacterium tumefaciens* strains LBA4404 containing the following vectors:

pBI101 (Clontech), which consists of the coding part of glucuronidase preceding the nopaline synthase terminator in binary vector pBIN19. This construction, hereafter called construction pBI101, is devoid of a promoter.

pBI221 (Clontech), which consists of a fragment of 800 base pairs of the 35S promoter of the cauliflower mosaic virus, inserted in front of the coding part of glucuronidase in vector pBI101. This construction will hereafter be called construction pBI221.

The kanamycin-resistant buds were then transferred to a medium for the induction of roots in the presence of carbenicillin and kanamycin. The plantlets are then potted up into a substrate composed of peat and vegetable mold and are grown on in a greenhouse. All the transformed plants (R0 generation) which have survived the steps of regeneration and greenhouse acclimatization were found to be morphologically normal and fertile. They were self-fertilized and gave seeds (R1 generation).

Section 16: Analysis of the genomic DNA of tobacco plants transformed with *Agrobacterium tumefaciens* containing plasmid pSG246 (R0 generation) by the Southern blotting technique The high-molecular tobacco genomic DNA was isolated from mature leaves of transgenic plants of the R0 generation by the method involving extraction with cetyltrimethylammonium bromide and purification by precipitation, described in the work "Plant Molecular Biology Manual" cited above.

10 μg of this genomic DNA were digested overnight at 37° C. with 20 units of the restriction enzymes HindIII and EcoRI. The restriction fragments obtained were separated by electrophoresis on agarose gel (1%). The DNA was transferred to a nylon filter (Hybond $N^+$, Amersham) by the Southern blotting method and hybridized with a nucleotide probe comprising part of the sequence of the recombinant gene. Labeled by coupling with peroxidase (ECL kit, Amersham). The membranes are then washed and developed according to the protocol recommended by Amersham.

Analysis of the films affords the following conclusions:

some plants do not possess copies of the transferred recombinant gene (absence of signal).

most of the plants tested contain at least one copy without rearrangement of the construction: 246C promoter/ coding sequence of β-glucuronidase/NOS terminator, hereafter called construction pSG246.

some profiles suggest that internal rearrangements exist in this construction, but these events are rare.

Section 17: Study of the activation characteristics of the 246C promoter in transgenic tobacco plants This study was performed on plants of the R1 generation which had previously been selected in vitro on Murashige and Skoog's agar medium containing 500 μg/ml of kanamycin.

10 plants per transformant lineage, selected for their kanamycin resistance, are pricked out into vegetable mold and then cultivated for 4 to 5 weeks in a culture chamber.

a) Activation by the phytopathogenic bacterium *Pseudomonas solanacearum*

Inoculation by infiltration

Inoculation tests are conducted according to the protocol described in section 1 on four leaves belonging to 2 different plants. The measurements of glucuronidase activity were made according to the method described by Jefferson (Plant Molecular Biology Reporter, 5, 387, 1987) using 4-methylumbelliferyl β-D-glucuronide as the substrate.

The results show that:

the plants containing construction pBI101 have no detectable glucuronidase activity.

the plants containing construction pBI121 have a glucuronidase activity of between 5000 and 70,000 pmol of methylumbelliferone/min/mg of protein, corresponding to an expected constitutive expression for this construction. A slight activation of this promoter in response to the stress of infiltration was found for some transformants.

the plants containing construction pSG246 have a low glucuronidase activity, in the non-inoculated plants, of between 2000 and 5000 pmol/mg of protein. A strong induction is measured in response to the bacterial infection, irrespective of the bacterial strain used (GMI1000 or K60 (Sequeira et al., Physiol. Plant Pathol., 10, 43, 1977), (compatible strain which causes symptoms). The induction factor (ratio of the activity measured after inoculation to the activity measured before inoculation) is of the order of 20 and the activity values sometimes exceed those obtained with the plants expressing construction pBI121.

Localized bacterial infection

A localized bacterial infection is produced by depositing a drop of a bacterial suspension of *Pseudomonas solanacearum* (3 μl containing 3×10⁵ bacteria obtained as described in section 1) onto a wound obtained by perforating a leaf with a syringe needle.

The 246C promoter is activated around the lesion created by the infection and also in all parts of the infected plant (inoculated leaf, upper leaves and lower leaves of the plant, and roots). This systemic activation takes place as from the first few hours after inoculation.

No activation was observed in plants of the R1 generation derived from plants transformed with constructions pBI101 and pBI121.

The same type of localized infection produced in the roots of tobacco plants cultivated in vitro again results in a strong activation of the promoter at the inoculation site, but also throughout the root and in the aerial part of the plant.

b) Activation by the pathogenic fungus *Chalara elegans*

In vitro study 10 to 15 ml of Murashige and Skoog's liquid medium are poured into a Petri dish containing a 3-week culture of *Chalara elegans* in the process of sporulation (culture on PDA (potato dextrose agar) medium, Difco).

The spores can be collected by scratching the surface of the culture. After counting, appropriate dilution makes it possible to obtain suspensions of $10^4$ and $10^5$ spores per ml.

7 ml aliquots are distributed into Magenta dishes (Sigma). A transgenic tobacco plant (about 3 weeks old and cultivated in a sterile medium), transformed with the β-glucuronidase gene under the control of the 246C promoter, is introduced into each dish, their roots dipping into the spore suspension. The plants are then removed and frozen and the glucuronidase activity is determined. At the time of infection, the specific activity is 20,000 pmol of methylumbelliferone per mg of protein. Compared with non-inoculated references placed under the same conditions, this activity is increased by factors of 8 and 8.5 for infections with $10^4$ and $10^5$ spores per ml, respectively, as from 4 days after inoculation.

Greenhouse study 10 plants per transformant: lineage, selected for their kanamycin resistance, are pricked out into 3×3 cm pots. When the 5th leaf appears, the plants are inoculated by depositing a suspension of $5×10^5$ endoconidia of *Chalara elegans* onto the neck.

c) Activation by the pathogenic fungus *Sclerotinia sclerotiorum*

Study on leaf disks

Leaf disks 20 mm in diameter, originating from plants expressing construction pSG246, are placed on an appropriate liquid survival medium. A cube of agar with a side length of about 5 mm, containing mycelium of *Sclerotinia sclerotiorum*, is placed on each of these disks. The glucuronidase activity, measured as a function of time, shows that the presence of mycelium induces the glucuronidase activity after 7 hours of contact. After 24 hours, the activity is increased by a factor of 4 compared with that of leaf disks not brought into contact with the mycelium. The same experiment carried out on leaf disks derived from reference tobaccos (not expressing construction pSG246) shows only a glucuronidase activity comparable to the background.

d) Activation by elicitors

Two types of elicitors were used, the one a biotic type corresponding to molecules derived from natural molecules or macromolecules, and the other an abiotic type corresponding to chemical molecules.

d1. Biotic elicitors of bacterial or fungal origin

The elicitors used are harpin, which is a protein isolated from *Erwinia amylovora*, and a protein isolated from *Pseudomonas solanacearum* culture supernatant. Protein elicitors such as cryptogeine isolated from *Pseudomonas cryptogea* and capsiceine isolated from *Pseudomonas capsici* (Ricci et al., 1989, Eur. J. Biochem., 183, 555–563) were similarly tested.

Using a syringe, appropriate concentrations of elicitors were infiltrated in all cases under the lower epidermis of tobacco leaves expressing construction pSG246. The induction of activity is induced in all cases by the presence of an elicitor in an approximately 5 mm ring immediately adjacent to the infiltration zone. The stimulation is very apparent 24 hours after infiltration but is visible after only 6 hours. The activity after 24 hours is often 5 to 6 times those of the reference plants (plants expressing construction pSG246 but without elicitors injected under the epidermis).

d2. Abiotic elicitors: salicylic acid, copper sulfate

Tobacco leaves expressing construction pSG246, which have been detached from the plant, are immersed in solutions with a salicylic acid concentration of 1 to 10 µg/ml or a copper sulfate concentration of 0.025 to 0.25 mM.

In the presence of salicylic acid, the glucuronidase activity is increased by a factor of 5 after 6 hours and 10 after 24 hours. In the case of copper sulfate, the glucuronidase activity is increased by a factor of 17 at 0.025 mM and 11 at 0.25 mM when compared with leaves of untreated reference plants.

d3. Induction by growth regulators

The application of an auxin in the form of 2,4-dichlorophenoxyacetic acid (2,4-D) was effected at concentrations of 1.5 and 10 µM. The application, effected by the immersion of petioles of detached tobacco leaves expressing construction pSG246, shows that induction in the leaf starts 6 hours after the application of auxin at a concentration of 5 µM and is stimulated 18-fold after 12 hours, compared with the leaves of reference plants not treated with auxin.

The glucuronidase activity is measured when the symptoms of the disease appear, i.e. about 15 days after inoculation.

The results of the activity measured on the aerial part of the whole plant show that:
- the plants containing construction pBI101 have no detectable glucuronidase activity.
- the plants transformed with construction pBI121 have an activity of 12,000 to 60,000 pmol of methylumbelliferone/min/mg of protein. This activity varies little after inoculation.
- the plants transformed with construction pSG246 have a low glucuronidase activity in the healthy plants. This activity increases considerably in the plants which display symptoms, reaching values of 85,000 pmol of methylumbelliferone formed/min/mg of protein.

e) Activation by a wound

This activation was investigated on leaves of about 5-week-old plants of the R1 generation containing construction pSG246, previously selected for their kanamycin resistance.

The simple excision of a leaf causes a slow and weak activation of the promoter, both in the leaf and in the plant; however, the laceration of a leaf causes a very large (5-fold) and extremely rapid (30 min) increase in the glucuronidase activity of the lacerated leaf.

f) Heat-shock activation

About 5-week-old tobacco plants of the R1generation containing construction pSG246, previously selected for their kanamycin resistance, are transferred for 2 or 4 h to an enclosure at 40° C. in order to cause a heat shock. When the treatment has ended, the plants are immediately frozen in liquid nitrogen and their β-glucuronidase activity is determined on the whole of the aerial part.

The same protocol is applied to plants transformed with construction pBI121; the activity of these plants is not modified by heat shock.

By contrast, the plants containing construction pSG246 exhibit a large increase in glucuronidase activity after heat shock; the mean stimulation factor, determined on several plants, is of the order of 12.

g) Expression during development, and spatial distribution of the expression in the plant The localization of the activity in the plant tissues can be visualized by using the histochemical substrate cyclohexylammonium 5-bromo-4-chloroindol-3-yl-β-D-glucuronide (X-gluc) for disclosing glucuronidase activity, according to the method described by Jefferson (Plant Molecular Biology Reporter, 5, 387, 1987).

Germination of the seeds

During the germination of tobacco seeds of the R1 generation expressing glucuronidase under the control of the 246C promoter, the expression is not detectable in the cotyledons, strong throughout the root and very strong in the root and cauline meristems. In the developed plant, the detection of glucuronidase activity was recorded in all the tissues tested, including the dry seed.

Section 18: Production of colza plants transformed with Agrobacterium rhizogenes containing plasmid pSG246

The transformation is effected according to the protocol of P. Guerche et al. (P. Guerche et al., 1987, Mol. Gen. Genet., 206, 382). The different culture media are those described by Pelletier et al. (Pelletier et al., 1983, Mol. Gen. Genet., 191, 244). Their composition will be given in detail below (Table 2).

a) Production of transformed roots

Stem segments are taken from the apical end of colza plants (Brassica napus: Brutor and Westar spring varieties and winter variety) about 1 m in height. These segments are sterilized on the surface, rinsed in sterile water, cut into segments of about 1.5 cm in length and placed in a tube containing medium A.

The end of this segment is inoculated by depositing a suspension of the Agrobacterium rhizogenes strain containing plasmid pSG246.

Transformed roots appear on the stem segment after 1 to 2 weeks; they are removed and placed on medium B containing agar (15 g/l) and complemented with 500 µg of cefotaxim/ml.

b) Regeneration of transformed plants

Root fragments are incubated for 15 days in medium D containing 3 mg/l of 2,4-dichlorophenoxyacetic acid and are then placed on medium RCC for inducing buds. Rooted plants are then obtained by transferring the buds to media F and G.

TABLE 2

Composition of the different media used for the production of transformed colza plants

| Composition (mg/l) | A | B | RCC | F | G | D |
|---|---|---|---|---|---|---|
| NH$_4$NO$_3$ | 1650 | | 1650 | 1650 | 825 | 200 |
| KNO$_3$ | 1900 | 2500 | 1900 | 1900 | 950 | 1250 |
| (NH$_4$)$_2$SO$_4$ | | 134 | | | | 67 |
| NaH$_2$PO$_4$ | | 150 | | | | 75 |
| KH$_2$PO$_4$ | 170 | | 170 | 170 | 85 | 5 |
| CaCl$_2$.2H$_2$O | 440 | 750 | 440 | 440 | 220 | 525 |
| MgSO$_4$.7H$_2$O | 370 | 250 | 370 | 370 | 185 | 250 |
| H$_3$BO$_3$ | 12.4 | 3 | 12.4 | 6.2 | 6.2 | 12.4 |
| MnSO$_4$.4H$_2$O | 33.6 | 10 | 33.6 | 22.3 | 22.3 | 33.6 |
| ZnSO$_4$.7H$_2$O | 21 | 2 | 21 | 8.6 | 8.6 | 21 |
| KI | 1.66 | 0.75 | 1.66 | 0.83 | 0.83 | 1.66 |
| Na$_2$MoO$_4$.2H$_2$O | 0.5 | 0.25 | 0.5 | 0.25 | 0.25 | 0.5 |
| CuSO$_4$.5H$_2$O | 0.05 | 0.025 | 0.05 | 0.25 | 0.25 | 0.05 |
| CoCl$_2$.6H$_2$O | 0.05 | 0.025 | 0.05 | 0.25 | 0.25 | 0.05 |
| FeSO$_4$.7H$_2$O | 22.4 | 27.8 | 27.8 | 27.8 | 22.24 | 27.8 |
| Na$_2$EDTA | 29.84 | 37.3 | 37.3 | 37.3 | 29.84 | 37.3 |
| Inositol | 100 | 100 | 100 | 100 | 100 | 100 |
| Nicotinic acid | 0.5 | 1 | 0.5 | 1 | 0.5 | 1 |
| Pyridoxine.HCl | 0.5 | 1 | 0.5 | 1 | 0.5 | 1 |
| Thiamine | | 10 | | 10 | | 10 |
| Glycine | 2 | | 2 | | 2 | |

TABLE 2-continued

Composition of the different media used for the production of transformed colza plants

| Composition (mg/l) | A | B | RCC | F | G | D |
|---|---|---|---|---|---|---|
| Glucose | 10,000 | 20,000 | | | 10,000 | |
| Sucrose | 10,000 | | 10,000 | 10,000 | | 20,000 |
| D-Mannitol | | 70,000 | 10,000 | | | |
| NAA | | 1 | 1 | 0.1 | 0.1 | |
| BA | | 1 | 0.5 | 0.5 | | |
| 2,4-D | | 0.25 | | | | 1 |
| Adenine sulfate | | | | | | 30 |
| IPA | | | | | | 30 |
| GA | | | | 0.02 | | |
| Tween 80 | | 10 | | | | |
| Agar | 8000 | | 8000 | 8000 | 8000 | |
| pH | 5.8 | 5.8 | 5.8 | 5.8 | 5.8 | 5.8 |
| Gentamycin (sulfate) | 10 | | | | | |

NAA: naphthaleneacetic acid
BA: 6-benzylaminopurine
2,4-D: 2,4-dichlorophenoxyacetic acid
IPA: $N^6$-(2-isopentyl)adenine
$GA_3$: gibberellic acid
EDTA: ethylenediaminetetraacetic acid Section 19: Characteristics of the expression of the glucuronidase gene under the control of the 246C promoter in colza plants a) Activation by a wound The leaves of colza plants of the R1 generation containing glucuronidase under the control of the 246C promoter were excised or excised and lacerated.

A weak activation of glucuronidase activity is observed in the excised leaves; a very strong (6 times the base activity) and extremely rapid (about 30 min) activation results from laceration.

b) Infection with phytopathogenic fungi

Leaf parasite (*Alternaria brassicae*):

Colza plants of the R1 generation possessing construction pSG246 are cultivated in vegetable mold for about 3 weeks in pots. The plants are then inoculated locally with a suspension of spores (10 ml containing 1000 spores obtained after culture on PDA medium) of the pathogenic fungus *Alternaria brassicae*, deposited on a wound made with a needle. Necrosis then develops around this wound.

A strong stimulation of the glucuronidase activity (detected by testing with X-gluc, section 17e) is then observed in the inoculated leaf, around the necrotic zone.

Root parasite (*Rhizoctonia solani*):

Colza seeds of the R1 generation, transformed with construction pSG246, are sown on a substrate consisting of a mixture of peat, vermiculite and sand (10:10:5, v:v), contained in a 1 liter pot. The seeds are covered with a 1 cm layer of substrate containing 10,000 viable propagules of *Rhizoctonia solani* per gram. These propagules are obtained by culturing a Rhizoctonia strain in a Roux flask on grains of rice for 15 days and then grinding it to a particle size of less than 1 mm.

During their development, the colza plants are attacked at the roots.

A strong stimulation of the glucuronidase activity (detected by testing with X-gluc', section 17e) is observed in the roots of infected plants, compared with the activity measured in the roots of control plants (same R1 lineage of transformed but not infected plants). Furthermore, a strong stimulation of the glucuronidase activity is induced systemically in the aerial parts.

c) Heat-shock activation of colza plants of the R1 generation

About 5-week-old colza plants of the R1 generation containing construction pSG246 are transferred for 2 or 4 h to an enclosure at 40° C. in order to cause a heat shock. When the treatment has ended, the plants are immediately frozen in liquid nitrogen and their β-glucuronidase activity is determined on the whole of the aerial part.

The same protocol is applied to plants transformed with construction pBI121; the activity of the latter plants is not affected by heat shock.

By contrast, the plants containing construction pSG246 exhibit a large increase in glucuronidase activity following heat shock; the mean stimulation factor, determined on several plants, is of the order of 12.

d) Expression during development

During the germination of colza seeds of the R1 generation containing glucuronidase under the control of the 246C promoter, an expression of this protein is observed in the cotyledons, a strong expression throughout the root and a very strong expression in the root and cauline meristems.

A very strong expression was also measured in the transformed roots and calli during the steps involving the regeneration of transgenic plants, as well as in the various parts of the plant (including the mature seeds).

Section 20: Production of sunflower calli transformed with *Agrobacterium rhizogenes* containing plasmid pSG246

The transformation is effected according to the protocol of Guerche et al. (Mol. Gen. Genet., 206, 382, 1987), which was initially developed for the transformation of colza. The different culture media are those described by Pelletier et al. (Mol. Gen. Genet., 191, 244, 1983); their composition has been described in detail (Table 2).

Sunflower hypocotyls are obtained by germinating seeds on vermiculite for 7 to 10 days. These seeds are placed in a culture clamber, the conditions being 16 h of illumination at 20° C./8 h of darkness at 17° C. The hypocotyls are sterilized on the surface, rinsed in sterile water and placed in a tube containing Murashige and Skoog's medium in which the concentration of macroelements has been reduced by half.

The end of this segment is inoculated by depositing a suspension of the *Agrobacterium rhizogenes* strain containing plasmid pSG246.

Transformed roots appear after one month; they are removed and placed on medium B containing agar (15 g/l) and complemented with 500 μg of cefotaxim/ml, for 4 weeks with weekly subculture. They are then cultivated in the same liquid medium, with agitation (100 rpm), and subcultured every month. Transfer of these roots to medium D enables calli to form from the transformed roots.

The glucuronidase activity of the roots cultivated in liquid medium B and calli cultivated on medium D, estimated by fluorimetry, has very high values of between $10^4$ and $10^5$ pmol of methylumbelliferone formed/min/mg of proteins.

Section 21: Transient expression of the glucuronidase gene under the control of the promoter of the 246C gene in immature sunflower embryos The immature embryos of field mother plants of genotype 105 were removed and cultured for 14 days on medium I (Table 3) at 25° C. in the dark. These embryos are then cultivated for 3 days on medium II at 25° C. under a photoperiod of 16 hours per day/8 hours per night. About twenty embryos, are then deposited side-by-side on medium III.

Preparation of vector pSG123:

This is carried out according to the protocol described in section 10.

Transformation of the plant material:

The plasmid DNA (vector pSG123) is introduced into the plant cells by using the particle gun constructed according to the principle described by Zumbrunn (Zumbrunn et al., 1989, Technique, 1(3), 204–216). The plasmid DNA is adsorbed onto tungsten microparticles at a rate of 4 µg/mg of tungsten. 2.5 mg of the tungsten/DNA mixture are then deposited onto a macroprojectile, which is accelerated by the explosion of a cartridge.

The break-up of the macroprojectile on a stop plate containing a hole enables the tungsten microparticles and the DNA to be projected into the cells.

Measurement of the transient expression:

The DNA adsorbed on the tungsten microparticles which have penetrated the plant cells is released; the chimeric gene associating the promoter of the 246C gene with the glucuronidase is then transcribed and subsequently translated. The glucuron: Ldase obtained is then visualized by the histochemical test described by JEFFERSON et al., 1987, Plant Molecular Biology Reporter, 5, 387, using the substrate cyclohexylammonium 5-bromo-4-chloroindol-3-yl-β-D-glucuronide (X-gluc). The cells expressing the gene then give a blue coloration.

Counting of the number of blue cells obtained per Petri dish during a transient expression experiment makes it possible to count the number of transformed cells and to estimate the expression of the chimeric construction tested.

The transient expression, measured using the substrate X-gluc 48 hours after bombardment with the microparticle gun, shows that the β-glucuronidase gene is expressed in the immature sunflower embryos.

The intensity is greater than that induced by using plasmid pBI221 (Clontech), in which the glucuronidase gene is placed under the control of the 35S promoter of the cauliflower mosaic virus.

The number of transformed cells expressing the glucuronidase gene under the control of the promoter of the 246C gene is of the order of 140 per dish (mean value over 4 experiments), whereas the number of transformed cells is 60 per dish (mean value over 4 experiments) in the presence of plasmid pBI221, in which the glucuronidase gene is placed under the control of the 35S promoter of the cauliflower mosaic virus.

The embryos are then drained on sterile filter paper and subsequently re-cultured on medium II in the dark for 3 days. The embryos are then briefly rinsed with Murashige and Skoog's liquid medium (Murashige and Skoog, 1962, Physiol. Plant, 15, 473) containing 500 mg/l of the antibiotic cefotaxim. They are then drained on sterile filter paper and cultured on medium III containing 250 mg/l of cefotaxim, 250 mg/l of carbenicillin and 50 mg/l of paromomycin. This culture is effected at 25° C. under a photoperiod of 16 h day/8 h night; the plant tissues are subcultured every 21 days on this same medium.

The buds newly formed from these tissues are transferred to medium IV under the same temperature and photoperiod conditions. The rooted plants are then grown on in a greenhouse.

Section 22: Expression of β-glucuronidase under the control of the 246C promoter in transformed sunflower plants The plants expressing construction pSG246 have a glucuronidase expression which is at least equal to that obtained with plants transformed with construction pBI121.

TABLE 3

Composition of the different media used for the production of transformed sunflower plants

| Medium | I | II | III | IV |
|---|---|---|---|---|
| $KNO_3$ | 2500 | 2500 | 1900 | 1900 |
| $NH_4NO_3$ | — | — | 1650 | 1650 |
| $CaCl_2.2H_2O$ | 150 | 150 | 440 | 440 |
| $MgSO_4.7H_2O$ | 250 | 250 | 370 | 370 |
| $KH_2PO_4$ | — | — | 170 | 170 |
| $(NH_4)_2SO_4$ | 134 | 134 | — | — |
| $NaH_2PO_4.H_2O$ | 150 | 150 | — | — |
| $ZnSO_4.7H_2O$ | 2 | 2 | 8.6 | 8.6 |
| $H_3BO_3$ | 3 | 3 | 6.2 | 6.2 |
| KI | 0.75 | 0.75 | 0.83 | 0.83 |
| $CuSO_4.5H_2O$ | 0.025 | 0.025 | 0.025 | 0.025 |
| $Na_2MoO_4.2H_2O$ | 0.25 | 0.25 | 0.25 | 0.25 |
| $CoCl_2.6H_2O$ | 0.025 | 0.025 | 0.025 | 0.025 |
| $MnSO_4.4H_2O$ | 10 | 10 | 22.3 | 22.3 |
| $Na_2EDTA$ | 37.3 | 37.3 | 37.3 | 37.3 |
| $FeSO_4.7H_2O$ | 27.8 | 27.8 | 27.8 | 27.8 |
| Nicotinic acid | 1 | 1 | 0.5 | 0.5 |
| Thiamine.HCl | 10 | 10 | 0.1 | 0.1 |
| Pyridoxine.HCl | 1 | 1 | 0.1 | 0.5 |
| Myoinositol | 4000 | 4000 | 100 | 100 |
| L-Glycine | — | — | — | 2 |
| L-Alanine | 1000 | 1000 | — | — |
| L-Glutamine | 800 | 800 | — | — |
| L-Serine | 160 | 160 | — | — |
| L-Tryptophan | 50 | 50 | — | — |
| L-Cysteine | 10 | 10 | — | — |
| Ca D-pantothenate | — | — | 0.8 | — |
| Folic acid | — | — | 0.1 | — |
| Choline chloride | — | — | 0.1 | — |
| p-Aminobenzoic acid | — | — | 0.05 | — |
| Riboflavine | — | — | 0.05 | — |
| Sucrose | 120,000 | 60,000 | 30,000 | 30,000 |
| 2,4-Dichlorophenoxyacetic acid | 2 | — | — | — |
| 6-Benzylaminopurine | — | 0.4 | — | — |
| Kinetin | — | — | 1 | — |
| Indolacetic acid | — | — | — | 0.05 |
| Agar | 7000 | 7000 | 7000 | 8000 |
| pH | 5.7 | 5.8 | 5.7 | 5.7 |

Section 23: Protocol of the expression of the β-glucuronidase gene under the control of the 246C promoter in monocotyledon tissues Production of the plant material:

Seeds of the GERBEL barley genotype are germinated on vermiculite in a greenhouse. After 7 days, the leaves and roots were removed and placed on a Petri dish containing Murashige and Skoog's agar medium for the transient expression experiments.

Immature maize embryos are removed, 10 to 14 days after pollination, from stools (line LH132) cultivated in a greenhouse. The embryos are placed with their embryonic axis in contact with the induction medium (composition given in Table 4 below) and then, 3 weeks later, on the maintenance medium (Table 5). The calli obtained are subcultured every week. The transient expression experiments are performed a few hours after subculture.

Preparation of vector pSG123:

This is carried out according to the protocol described in section 10.

Transformation of the plant material:

The plasmid DNA (vector pSG123) is introduced into the plant cells by using the particle gun constructed according to the principle described by Zumbrunn (Zumbrunn et al., 1989, Technique, 1(3), 204–216). The plasmid DNA is adsorbed onto tungsten microparticles at a rate of 4 µg/mg of tungsten. 2.5 mg of the tungsten/DNA mixture are then deposited onto a macroprojectile, which is accelerated by the explosion of a cartridge.

The break-up of the macroprojectile on a stop plate containing a hole enables the tungsten microparticles and the DNA to be projected into the cells.

Measurement of the transient expression:

The DNA adsorbed on the tungsten microparticles which have penetrated the plant cells is released; the chimeric gene associating the promoter of the 246C gene with the glucuronidase is then transcribed and subsequently translated. The glucuronidase obtained is then visualized by the histochemical test described by JEFFERSON et al., 1987, Plant Molecular Biology Reporter, 5, 387, using the substrate cyclohexylammonium 5-bromo-4-chloroindol-3-yl-β-D-glucuronide (X-gluc). The cells expressing the gene then give a blue coloration.

Counting of the number of blue cells obtained per Petri dish during a transient expression experiment makes it possible to count the number of transformed cells and to estimate the expression of the chimeric construction tested.

TABLE 4

| Medium for inducing maize calli from immature embryos (in mg per liter) | |
|---|---|
| MgSo$_4$.7H$_2$O | 370 |
| CaCl$_2$.2H$_2$O | 440 |
| KNO$_3$ | 1900 |
| NH$_4$NO$_3$ | 1650 |
| KH$_2$PO$_4$ | 170 |
| Na$_2$MoO$_4$.2H$_2$O | 0.25 |
| CuSO$_4$.5H$_2$O | 0.025 |
| MnSO$_4$.H$_2$O | 16.75 |
| H$_3$BO$_3$ | 6.2 |
| ZnSO$_4$.7H$_2$O | 8.6 |
| KI | 0.83 |
| CoCl$_2$.6H$_2$O | 0.025 |
| FeEDTA | 65.1 |
| Sucrose | 20,000 |
| Casein hydrolyzate | 100 |
| L-Proline | 5800 |
| Glycine | 2 |
| Nicotinic acid | 0.5 |
| Pyridoxine.HCl | 0.5 |
| Inositol | 100 |
| Thiamine.HCl | 0.1 |
| Abscisic acid | 0.06 |
| Chloramben | 4.12 |
| Phytagel | 3000 | pH = 5.7; autoclaving for 20 min at 12° C.

TABLE 5

| Medium for maintaining waize calli (in mg per liter) | |
|---|---|
| MgSo$_4$.7H$_2$O | 370 |
| CaCl$_2$.2H$_2$O | 440 |
| KNO$_3$ | 1900 |
| NH$_4$NO$_3$ | 1650 |
| KH$_2$PO$_4$ | 170 |
| Na$_2$MoO$_4$.2H$_2$O | 0.25 |
| CuSO$_4$.5H$_2$O | 0.025 |
| MnSO$_4$.H$_2$O | 16.75 |
| H$_3$BO$_3$ | 6.2 |
| ZnSO$_4$.7H$_2$O | 8.6 |
| KI | 0.83 |
| CoCl$_2$.6H$_2$O | 0.025 |
| FeEDTA | 65.1 |
| Sucrose | 20,000 |
| Casein hydrolyzate | 100 |
| L-Proline | 2900 |
| Glycine | 2 |
| Nicotinic acid | 0.5 |
| Pyridoxine.HCl | 0.5 |
| Inositol | 100 |
| Thiamine.HCl | 0.1 |

TABLE 5-continued

| Medium for maintaining waize calli (in mg per liter) | |
|---|---|
| Dicamba (Banvel ®) | 0.002 |
| Gelrite | 3000 | pH = 5.7; autoclaving for 20 min at 120° C.

Section 24: Transient expression of the β-glucuronidase gene under the control of the promoter of the 246C gene in barley tissues and maize calli The transient expression, measured using the substrate X-gluc 48 hours after bombardment with the microparticle gun, shows that the β-glucuronidase gene is expressed in barley leaves and roots and also in maize calli.

The intensity of the expression is as great as that induced by using plasmid pBI221 (Clontech), in which the glucuronidase gene is placed under the control of the 35S promoter of the cauliflower mosaic virus.

The promoter of the tobacco 246C gene is therefore capable of directing the expression of a gene in monocotyledons.

Section 25: Construction of a plasmid placing the tomato-tobacco chitinase gene under the control of the inducible promoter, and expression thereof in tobacco a) Preparation of the promoter sequence Plasmid pSG123, described above, is digested with the endonucleases HindIII and ScaI. After agarose gel electrophoresis, the HindIII-ScaI fragment of 2088 base pairs, containing the whole of the inducible promoter except for the 57 base pairs; located immediately upstream from the ATG, is purified Ligation of this purified fragment, the synthetic ScaI-BamHI oligonucleotide of 62 base pairs of the sequence [SEQ ID NO: 15] and a vector pTZ19R (Pharmacia), linearized with the endonucleases HindIII and BamHI, produced plasmid pPH111.

The HindIII-BamHI fragment of 2150 base pairs, containing the inducible promoter in its entirety, is isolated from this plasmid pPH111 by cleavage with the endonucleases HindIII and BamHI, followed by agarose gel electrophoresis.

b) Preparation of the fragment carrying a hybrid gene coding for a protein with endochitinase activity The BamHI-EcoRI fragment originating from plasmid pBR1 described in patent application EP-493 581, Example 1, and containing a chimeric gene coding for a protein with endochitinase activity [SEQ ID NO: 16], which comprises the sequence coding for a tomato-tobacco hybrid endochitinase (in position 438–1587) and the NOS terminator, is purified.

c) Cloning into binary vector pBIN19 T4 DNA ligase was used to ligate the promoter sequence (cf. above), the sequence coding for chitinase and the terminator sequence to binary vector pBIN19 (Bevan, 1984, Nucl. Acids Res., 12, 8711–8721), opened with the endonucleases HindIII and EcoRI. This vector carries two kanamycin resistance genes, the one being capable of expression in bacteria and the other, located immediately upstream from the complete recombinant gene, being capable of transfer to plant cells.

The vector obtained, called pBR20, is cloned into *E. coli* strain HB101 (Clontech).

2) Transformation of *Agrobacterium tumefaciens*

The transformation of *Agrobacterium tumefaciens* strain LBA4404 (Clontech) is effected by the freeze-thaw method described in Plant Molecular Biology Manual (Gelvin et al., op. cit.) (summarized in section 14), starting from 1 mg of plasmid pBR20.

3) Transformation of tobacco

Tobacco, *Nicotiana tabacum*, cultivated in vitro, was infected with *Agrobacterium tumefaciens* containing plasmid pBR20 according to the procedure of Horsch et al., which is well known to those skilled in the art (Horsch R. B. et al., 1985, Science, 227, 1229–1231) and the principal steps of which are explained below.

Leaf disks from axenic tobacco plants, *Nicotiana tabacum* (Wisconsin Havana 38 variety), are incubated in a culture of *A. tumefaciens* containing plasmid pBR20. The disks, drained on Whatman paper, are cultured on culture media in Petri dishes for multiplication of the transformed cells to give calli. These calli are then transferred to a medium containing 500 mg/ml of cefotaxim for decontaminating the plant tissues (elimination of the *Agrobacterium tumefaciens*) and 100 mg/ml of kanamycin for selecting the transgenic material.

Demonstration of the expression of the protein with endochitinase activity in transgenic tobaccos a) Preparation of the crude protein extracts from transformed tobacco The crude protein extracts were prepared from different plant tissues (root, stem, leaf, etc.). The tissue fragments were frozen in liquid nitrogen, reduced to powder and stored at −20° C. The powder was extracted at 4° C. in the presence of 0.1M ammonium acetate buffer of pH 5.2 and centrifuged at 10,000 g. The concentration of total proteins was determined on the supernatants, hereafter called the crude protein extracts, by Bradford's technique (Bradford, M. M., 1976, Anal. Biochem., 72, 248–254).

b) Demonstration of the existence of the hybrid chitinase by immunoblotting (Western blotting)

The crude protein extracts are subjected to Western blotting, a technique well known to those skilled in the art and described by H. Towbin et al. (Proc. Ntl. Acad. Sci. USA, 76, 1979, 4350–4354).

The immunodetection of the protein of interest is effected by means of an immune serum containing polyclonal antibodies recognizing the hybrid protein with chitinase activity (cf. EP-493 581, section 5).

The antigen-antibody complex is then revealed by means of a streptavidin-biotin system conjugated with alkaline phosphatase, using the RPN23 kit from Amersham (blotting detection kit) in accordance with the manufacturer's instructions.

The blot obtained shows, for the leaves of tobacco plants transformed with plasmid pBR20, the presence of a protein with an apparent molecular weight of about 26±6 kDa, which is recognized by the polyclonal antibodies and is absent from the leaves of the reference tobacco plants. This protein has the same apparent molecular weight as the hybrid protein with chitinase activity described in patent application EP-493 581.

Section 26: Localization of the minimum sequences of the 246C promoter which are responsible for the described characteristics Starting from vector pSG123 associating the promoter of the 246C gene with the β-glucuronidase gene, different deletions were generated in the 5' region of this promoter by using either restriction enzymes and/or nuclease Exo3. The precise extent of the deletions was determined by sequencing according to Sanger's method. FIG. 3 shows the different vectors obtained with the aid of these deletions of the 5' part of the promoter, counting from the transcription initiation site in position 2068.

a. Study of the strength of the 246C promoter by transient expression in tobacco protoplasts These vectors were used in transient expression on tobacco protoplasts which do not receive any effector. Analysis of the results shows that the maximum expression is obtained with vectors pSG251 and pSG33, reaching 30,000 pmol of methylumbelliferone formed/min/mg of protein. Larger deletions generated in this promoter (corresponding to vectors pSG29, pSG23, pSG451, pSG2, pSG24, pSG3, pSG1) have the effect of reducing the glucuronidase expression in proportion to the size of the deletion (Table below).

| Successive deletions of pSG123 Reference | GUS activity (pmol/min/mg) 0 |
| --- | --- |
| pBI221 | ≈1000 |
| pSG123 | 5000 |
| pSG251 | 29000 |
| pSG33 | 31000 |
| pSG29 | 26000 |
| pSG23 | 22000 |
| pSG451 | 10000 |
| PSG2 | 4000 |
| PSG14 | 1000 |
| pSG3 | 0 |
| PSG1 | 0 |

Vectors pSG251 and pSG33 corresponding to the promoters comprising the sequence (B) |vector pSG33| and the sequence (C) [vector pSG251] respectively.

b. Study of the strength of the promoter by the stable expression of chimeric constructions containing deleted promoters in transgenic tobaccos For each of the vectors described in FIG. 3, the chimeric gene associating the promoter (complete or truncated) with the coding part of glucuronidase and the NOS terminator was purified on agarose gel after cleavage with the restriction endonucleases HindIII and EcoRI. In each case, the chimeric gene was introduced into and ligated to binary vector pBIN19 (Clontech), previously opened at the HindIII and EcoRI sites (section 13).

Tobacco, *Nicotiana tabacum*, cultivated in vitro, was infected with *Agrobacterium tumefaciens* containing the different constructions described above. The procedure followed is that described in section 15.

The glucuronidase activity is the mean of the measurements made on 10 to 20 independent transformants. In the absence of an inducer, the base glucuronidase activity of the different genotypes is not substantially affected by the deletions for the constructions ranging from pSG251 to pSG451: it is substantially identical to that of genotypes containing construction pSG123 (FIG. 3). For constructions pSG2, pSG24, pSG3 and pSG1, on the other hand, the expression becomes weaker as the length of the promoter becomes shorter, the expressions for pSG3 and pSG1 being zero.

In the presence of bacterial inducers (see section 17), the expression of the plants containing constructions pSG251 and pSG33 is stimulated by a factor of 3 relative to construction pSG123. This indicates that the deleted part corresponding to the sequence D [SEQ ID NO: 6] contains a sequence which reduces the inducibility of the 246C promoter; by contrast, the sequence B |SEQ ID NO: 4], by itself or in the presence of the sequence C [SEQ ID NO: 5], affords a greater inducibility than the sequence of the 246C promoter (sequences B+C+D).

On the other hand, the expression is unchanged for the genotypes containing constructions pSG29 and pSG23 relative to the genotypes containing constructions pSG123.

For the genotypes containing constructions pSG451, pSG2, pSG24, pSG3 and pSG1 , the inducibility is systematically less than those of the genotypes containing construction pSG123: it becomes weaker as the promoter becomes shorter and is zero for the plants containing constructions pSG3 and pSG1.

These results indicate that the sequence D [SEQ ID NO: 6] contains information of the silencer type, which partially inhibits the inducibility of the complete promoter (sequences B+C+D).

What is claimed is:

1. A plant promoter, which comprises the sequence (B) [SEQ ID NO: 4] below:

TCAAATGAAA TACACATAAG AAGCACATAA

ATTTAAATGC CGTATTAAAC TTACAGTATA    60

CTATAGCGGA AGTTGGCTTG ATAAAGGAAC

GCTGAGGAGA GTAGCCGATG GTGAAACACT    120

AACATCAAGT GCAAAAGAAA GAAAAACTGA

AAACAGAAGA TGAATGTTTG AAGTGGGTAA    180

AAGATTACTT AAAAGATAGG TTTGGTTAAC

AAATGATTGT GACTGTTACG AAGCAGTGTG    240

AACCGTTGGG ACTTTTAATA TTCTTCGGCA

GAAGAACATT GCTCTTTCAA CGTATGTAGT    300

CTTTGTCTAC TTGTAGTTTT TTTTAATTTA

AATTAAATAA GTTAATTAGA GAAATAATAA    360

GAAGGATATT TTAGTAATTC AACTTTTAAC

TTTTAGGTTT CCCACTTATA ATATAATATA    420

GATATAGTTT TTTTTAATTT AAATTAAATA

AGTTAATTAG AGAAATAATA AGAAGGATAT    480

TTTAGTAATT CAACTTTTAA CTTTTAGGGT

TTCCACTTAT AATATAATAT AGATATAGAT    540

ATAGATATAG ATATAGATAA AGATATATAG

ATATAGATAG ATAATATAGA TGGATGAGTC    600

ATTGGCGATA AAGTGAGGAT TGTTTCATTT

TTGTTATTAA AAACTTACTA CTCCTTAAAT    660

ATAAAATATG ATTCCTTTTA AAAAAGAAAT

AGAATAAAAA TAAAGATAAA ACACTAAAAA    720

TAAATTAATT GTCTAGACAA AATCTACCGT

TCACCTCAAT TAATACACAT CCCCGTCCAC    780

ATCATGAAGT AGCTAGCACA AGCGTACAGA

TCAGTTGAAA GAAGAAAAGG GTCCAGTCCT    840

AAATATCCAA ATGTTCATGA AAGGAGGACA

ACTTAGTTTT TTCTACTAGA AAGAATATTT    900

TGACGAATTT CGTTCACATT GGCATGCTTT

AATTATATTA AGTAGTCTTT CTTGGAAAAG    960

AAGTATTTGC AATATCAAAC CAAATCTTCC

CATTACGCAA GCAATGACAT CTAAGCAAAT    1020

ATATATCACT ATAAATAGTA CTACTAATGT

TCAATGACTT TTATAAGCAC TACATATATA    1080

T ACTCAAACA AAAAGA    1096 or a sequence having a degree of homology of at least 80% with the sequence (B) and being inducible in stress situations.

2. A promoter according to claim 1 which comprises, upstream from the sequence (B), the sequence (C) [SEQ ID NO: 5] below:

| | | | | | | | |
|---|---|---|---|---|---|---|---|
| CCTTTTTCGA | TTCTAATCCA | ATCAATTCAA | CAGTGTAAGG | TGAAGCAGTC | AATTTAAAGG | 60 |
| AAGGCCTTTA | AATTCTAAAA | TATTGTACTT | TTCCTGCGCT | TCTAAAAGTG | AACGACAAAG | 120 |
| AAAAAATAGT | TATTCTTGAA | CTTAATATTG | TACAATAGGA | TAAATTTTAA | CTATCTATAA | 180 |
| AAAGAGAACA | AAACCTTAAT | CTCTTCAAAA | TAATATTATA | AGAAGTAACA | TAATTG | 236 | or a sequence having at least 80% of homology with sequence (C), the resulting promoter being inducible under stress situations.

3. A promoter according to one of claims 1 or 2 which comprises, upstream from the sequence (B), the sequence (D) [SEQ ID NO: 6] below:

| | | | | | | | |
|---|---|---|---|---|---|---|---|
| GAGCTCGGCA | AGGCTGACCA | AAGTCACAGA | AGCGATTGGA | ATTCGCAGGA | CAGACCATGC | 60 |
| ACCTGCGCAC | AAAATGTCGT | AGGTGCGACA | CACCAGAACC | AGCACTGGGC | AGCAGGTTTC | 120 |
| AATTGCTCTG | TGGCTCGTTT | GAAACTCATC | CGAGCCACTC | ATGACCTCGT | CCGAATATTT | 180 |
| CAACAAGTCC | ATAAACATAA | TACGGACATA | CTCGGGGTTT | CACTTCACGT | CAAACAACAT | 240 |
| CAAAATTACA | AATCACACCC | CGATTCGAAC | CTTGAGTTTT | AAACTTTTCA | ATTTGCAAAT | 300 |
| CTCGTGCCAA | AACATATTAA | ATGAATCCGG | AATGACTTCA | AATTTATAAA | TGACATAACG | 360 |
| GAGTTGTTCA | AATTTCCAGA | ATCAGATTCT | GCCTTTGATA | TCAAAAAGTC | AACCCCGTGA | 420 |
| TCAAACTTGG | AATTCTTTAG | CCTTTAAATT | GCTAGTTTTC | GTTAAATGGT | CATAACTTGA | 480 |
| GCTATGGACC | TCCAAATTAA | ATTTCGGGCA | TACGCTCAAA | TCCCAATTAC | GAATACGGAG | 540 |
| CTACCGGACT | GTCAAAATAC | TGATCCGGGT | CCGTTTGCTA | AAAACGTTGA | CCAAAGTCCA | 600 |
| CTAAGTTGAG | TTTTAAAACT | TTATTTCACA | TTTTAATCCA | TTTTTTACAT | GAAAACTTTC | 660 |
| CGGAAAATAC | GGAGTATGCA | CGCAAGTCGA | GGAATGATAA | ATGGTACGTT | TCGAAGTTTT | 720 |
| AGAACTCAAA | ATTACTTATT | AAATTTAAAG | ATGACATTTT | GGGTCATCAC | ATTGATGAAA | 780 |
| ATTTTGACAT | TAATATCTGA | GAACTTTCTT | TGA | | | 813 | or a sequence having at least 80% of homology with sequence (D), the resulting promoter being inducible under stress situations.

4. A process for obtaining the superexpression of a protein of interest in a plant in a stress situation, comprising:
introducing into plant cells a vector for the expression of a protein of interest, said vector comprising the promoter according to claim 1 or claim 2;
regenerating the plant cells into whole plants;
selecting plants which have integrated the above vector; and
cultivating said plants to obtain the superexpression of the protein of interest.

5. A process for obtaining the superexpression of a protein of interest in a plant in a stress situation, comprising:
introducing into plant cells a vector for the expression of a protein of interest, said vector comprising the promoter according to claim 3;
regenerating the plant cells into whole plants;
selecting the plants which have integrated the above vector; and
cultivating said plants to obtain the superexpression of the protein of interest.

6. Plant cells or microorganism cells which have integrated a vector for the expression of a protein comprising the plant promoter according to one of claims 1 or 2.

7. Plant cells or microorganism cells which have integrated a vector for the expression of a protein comprising the plant promoter according to claim 3.

8. A plant or part of a plant, which comprises plant cells according to claim 6.

9. A plant or part of a plant, which comprises plant cells according to claim 7.

10. A seed, which comprises plant cells which have integrated the plant promoter according to one of claims 3 or 4.

11. A seed comprising plant cells which have integrated the plant promoter according to claim 8.

12. A process for identifying a gene that induces natural defense reactions in plants against phytopathogenic or phytophagic organisms, comprising:
introducing into plant cells a vector comprising the promoter according to claim 1 or claim 2, operably linked to a gene to be tested;
regenerating the plant cells into whole plants;
selecting the plants or parts of plants which have integrated the above vector; and
testing the plants or parts of plants for induction of natural defense reactions upon infection with phytopathogenic or phytophagic organisms.

13. A process for preparing plant clones with enhanced natural defense reactions against phytopathogenic or phytophagic organisms comprising:
introducing into plant cells a vector comprising the promoter according to claim 1 or claim 2, operably linked to a gene to be tested;
regenerating the plant cells into whole plants;
selecting the plants or parts of plants which have integrated the above vector and which have enhanced natural defense reactions against phytopathogenic or phytophagic organisms; and
preparing plant clones from said plants or parts of plants.

* * * * *